United States Patent [19]

Jagpal

[11] Patent Number: 5,695,479
[45] Date of Patent: *Dec. 9, 1997

[54] INSTRUMENT, SYSTEM, KIT AND METHOD FOR CATHETERIZATION PROCEDURES

[76] Inventor: Ravindar Jagpal, 7301 Parkshire Ave., Dallas, Tex. 75231

[*] Notice: The portion of the term of this patent subsequent to Nov. 2, 2010, has been disclaimed.

[21] Appl. No.: 146,495

[22] Filed: Nov. 1, 1993

[51] Int. Cl.$^6$ .................................................. A61M 5/00
[52] U.S. Cl. ........................................................ 604/264
[58] Field of Search ........................... 604/164, 162, 604/171, 104, 264, 280, 272, 27, 53, 281–284

[56] References Cited

U.S. PATENT DOCUMENTS

| | | | |
|---|---|---|---|
| 1,527,291 | 2/1925 | Zorraquin . | |
| 2,001,638 | 5/1935 | Tomsjo | 128/347 |
| 2,623,521 | 12/1952 | Shaw | 128/221 |
| 2,952,256 | 9/1960 | Meader et al. | 604/272 |
| 3,099,988 | 8/1963 | Ginsberg | 604/272 |
| 3,386,438 | 6/1968 | Staians | 604/272 |
| 3,993,079 | 11/1976 | Henriques de Gatztan | 604/164 |
| 4,192,302 | 3/1980 | Boddie | 128/214 R |
| 4,280,503 | 7/1981 | Ackerman | 128/419 P |
| 4,327,723 | 5/1982 | Frankhauser | 128/214.4 |
| 4,335,718 | 6/1982 | Calabrese | 604/272 |
| 4,403,617 | 9/1983 | Trotinyak | 128/754 |
| 4,515,593 | 5/1985 | Norton | 604/265 |
| 4,525,157 | 6/1985 | Vaillancourt | 604/52 |
| 4,540,404 | 9/1985 | Wolvek | 604/96 |
| 4,581,019 | 4/1986 | Covelaru et al. | 604/164 |
| 4,652,256 | 3/1987 | Vaillancourt | 604/52 |
| 4,654,031 | 3/1987 | Lentz | 604/272 |
| 4,655,750 | 4/1987 | Vaillancourt | 604/165 |
| 4,675,004 | 6/1987 | Hadford et al. | 604/272 |
| 4,763,671 | 8/1988 | Goffinet | 128/786 |
| 4,781,676 | 11/1988 | Schweighardt et al. | 604/21 |
| 4,808,168 | 2/1989 | Warring | 604/158 |
| 4,844,092 | 7/1989 | Rydell et al. | 128/772 |
| 4,898,583 | 2/1990 | Borsanyi et al. | 604/153 |
| 4,935,008 | 6/1990 | Lewis, Jr. | 604/164 |
| 4,993,707 | 2/1991 | Ishihara | 604/272 |
| 4,995,866 | 2/1991 | Amplatz et al. | 604/83 |
| 5,011,478 | 4/1991 | Cope | 604/264 |
| 5,069,662 | 12/1991 | Bodden | 604/4 |
| 5,078,689 | 1/1992 | Keller | 604/164 |
| 5,098,410 | 3/1992 | Kerby et al. | 604/284 |
| 5,158,545 | 10/1992 | Trudell et al. | 604/164 |
| 5,205,829 | 4/1993 | Litochy | 604/264 |
| 5,242,410 | 9/1993 | Melker | 604/164 |
| 5,257,979 | 11/1993 | Jagpal | 604/104 |
| 5,290,244 | 3/1994 | Moonka | 604/164 |
| 5,383,859 | 1/1995 | Sewell, Jr. | 604/164 |

OTHER PUBLICATIONS

"Fabrication and Clinical Application of Intrahepatic Arterial Catheter Facilitating Repeated Infusion Therapy and Experience", Y Une, et., *Gan To Kagaku Ryoho (Japan)* Aug. 1988 (8 Pt 2) pp. 2379–2383.

(List continued on next page.)

*Primary Examiner*—Manuel Mendez
*Attorney, Agent, or Firm*—John W. Montgomery

[57] ABSTRACT

A system and method of catheterization, includes a needle, a "Y" chamber, a syringe or other chamber, a dilator, a sheath, a protective sleeve and a shock sheath. This introduces a comprehensive, uniform and universal approach to catheterization. Discriminatory methods of treatment using the invention are described. Particular attention has been paid to current problems in catheterization and the prevention of transmission of communicable diseases from patient to practitioner and vice-versa (e.g., the risk of contracting the HIV virus is substantially reduced using this system and method.) The discriminatory treatment of diseases, in particular, cancer, is now rapid, safe and in some instances, novel! The invention makes possible substantial reductions in the cost of health-care while improving the efficiency of diagnosis and treatment. The invention allows the practitioner to perform simultaneous diagnosis and treatment of diseases using the same procedure, regardless of their location in or on the body. The number and duration of hospitalizations is minimized, and the quality of life and length of survival for the patient are improved.

55 Claims, 11 Drawing Sheets

OTHER PUBLICATIONS

"Efficacy of an Attachable Subcutaneous Cuff for the Prevention of Intravascular Catheter–Related Infection", R. H. Flowers, III, et al., *JAMA*, Feb. 10, 1989, vol. 261, No. 6, pp. 878–883.

"An Overview of Interstitial Brachytherapy and Hyperthermia", Beverly B. Brandt and James Harney, *Oncology Nursing Forum*, vol. 16, No. 6, pp. 833–841, 1989.

"Catheter–Related Sepsis: Prospective, Randomized Study of Three Methods Long–Term Catheter Maintenance", Steven Eyer, M.D., et al., *Critical Care Medicine*, vol. 18, No. 10, pp. 1073–1079 Oct. 1990.

"Central Venous Catheter Related Sepsis: A Clinical Review", Chaim Putterman, *Resuscitation*, 20 (1990), 1–16.

"Clinical Predictors of Infection of Central Venous Catheters Used for Total Parenteral Nutrition", Carl W. Armstrong, M.D., et al., *Infect Control Hosp Epidemiol* 1990, vol. 11, No. 2, pp. 71–78.

"Preventing Central Venous Catheter–Related Complications", Thomas R. Beam, Jr., M.D., et al., *Infections in Surgery*, Oct. 1990, pp. 1–13.

"The Pathogenesis and Epidemiology of Catheter–Related Infection With Pulmonary Artery Swan–Ganz Catheters: A Prospective Study Utilizing Molecular Subtyping", Leonard A. Mermel, D.O., Sc.M., et al., *The American Journal of Medicine*, vol. 91 (suppl 3B), Sep. 16, 1991, pp. 197s–205s.

"Arrow–Howes Multi–Lumen Catheter With Antiseptic Surface and Vitacuff", *Arrow International Technical Report*, 1990.

"Air Emboli: A Potentially Lethal Complication of Central Venous Lines", Jackie Bretz Thielen, R.N., M.S.N., C.C.R.N., *Focus on Critical Care.AACN*, vol. 17 Num. 5, Oct. 1990, pp. 374, 378–380, 382–383.

"Central Venous Air Embolism Without a Catheter", Karl A. Poterak, M.D., Anil Aggarwal, M.D., *Canadian Journal of Anaesthesia 1991*, vol. 38:3, pp. 338–340, Apr. 1991.

"Late Radiation Damage in Normal Tissue", Elizabeth L. Travis, PhD, Kathryn A. Mason, MSC, *The Cancer Bulletin*, vol. 44, No. 2, pp. 105–110, 1992.

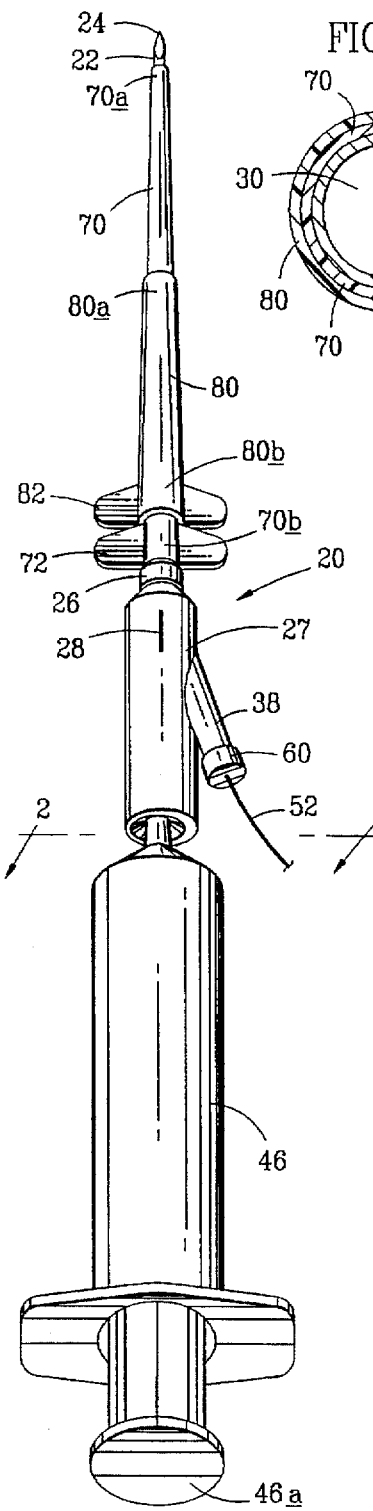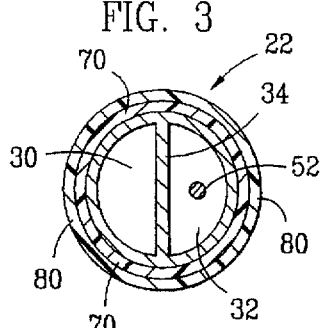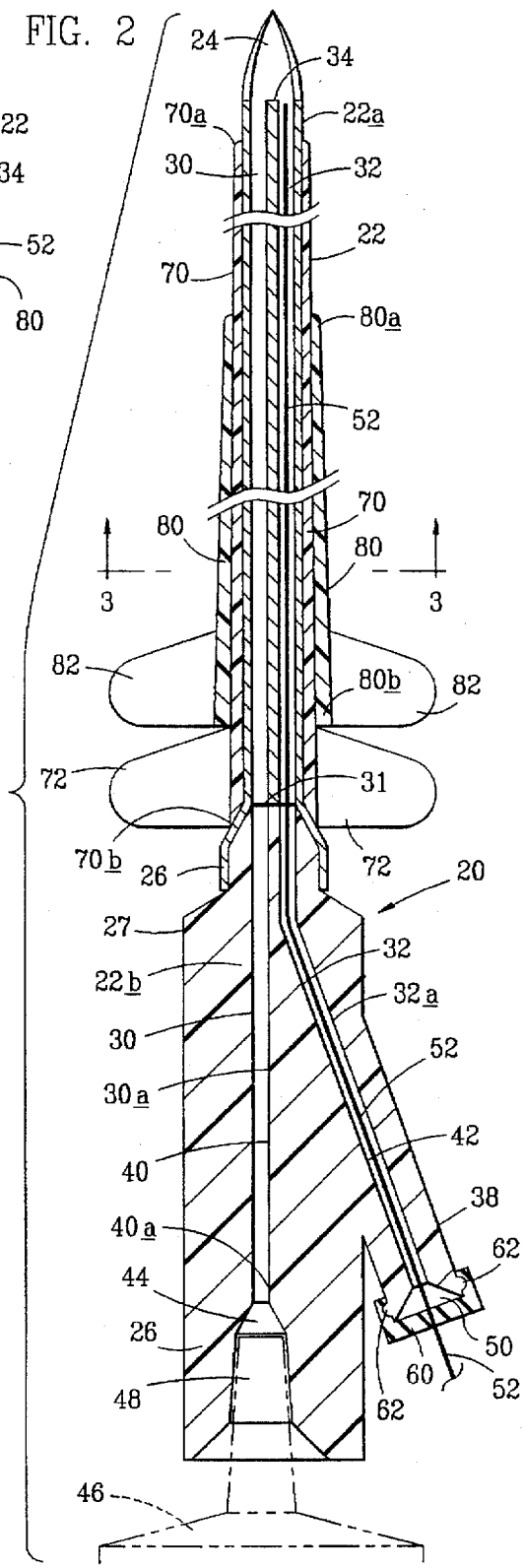

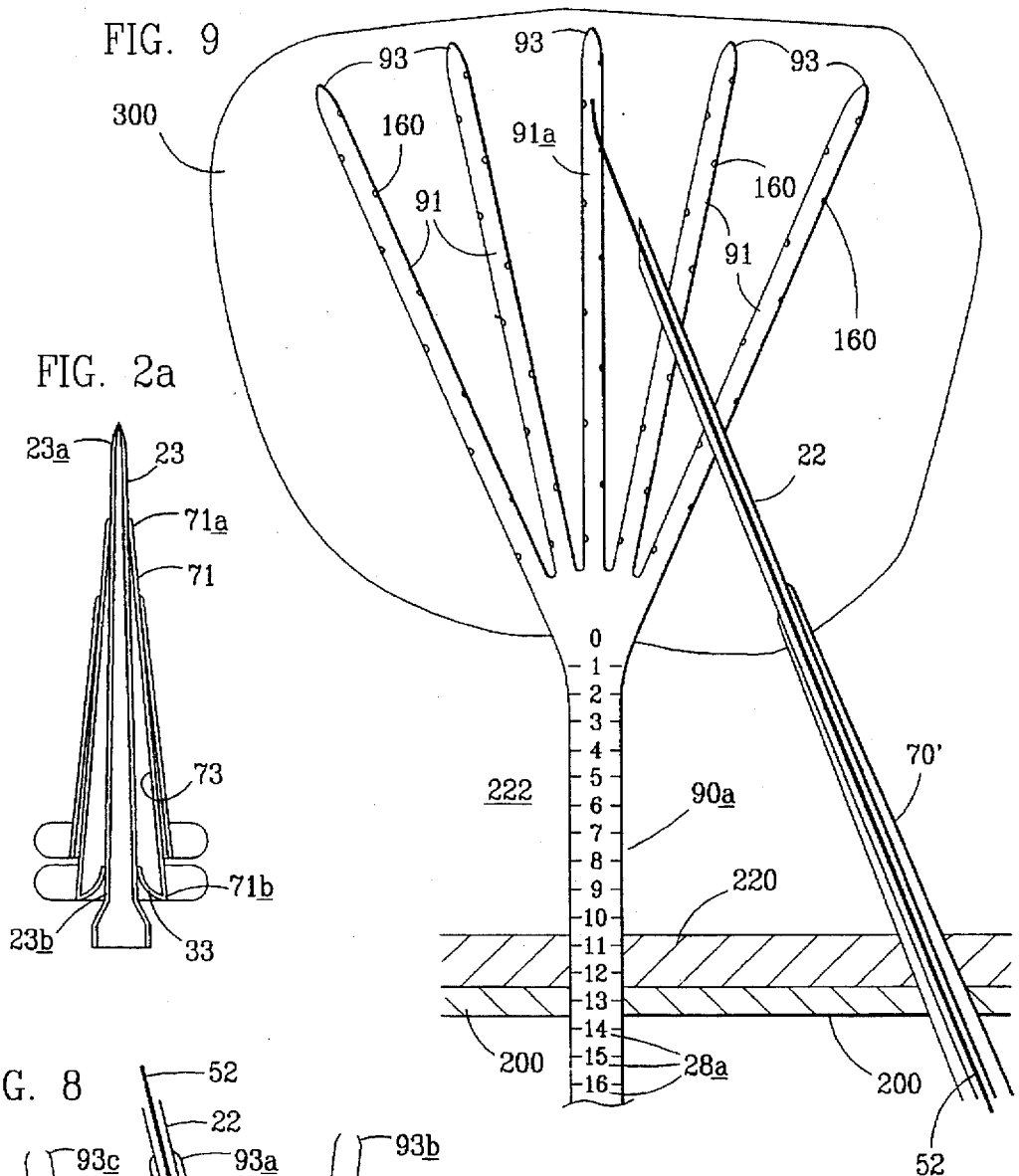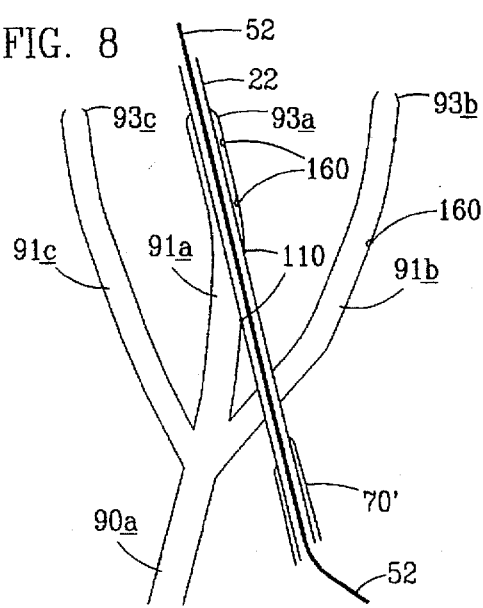

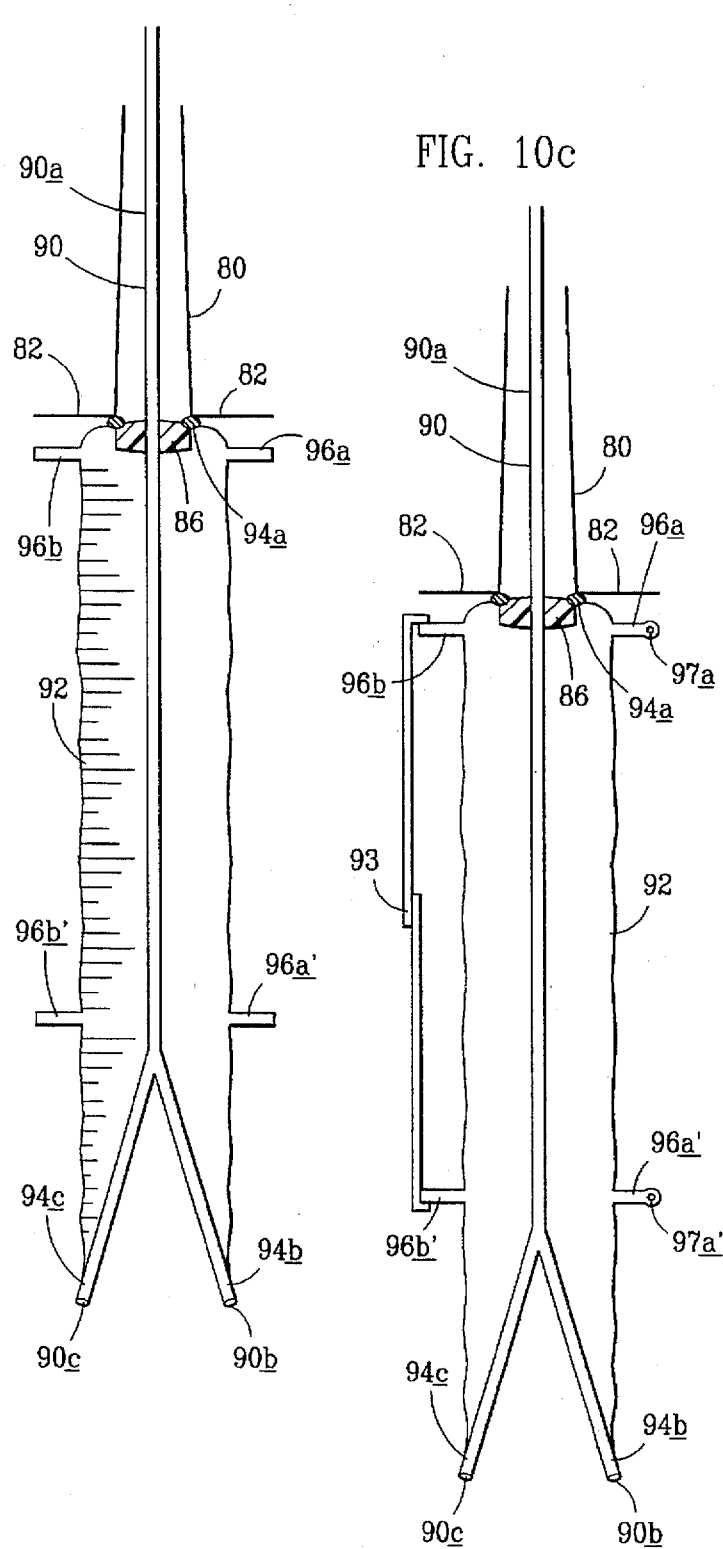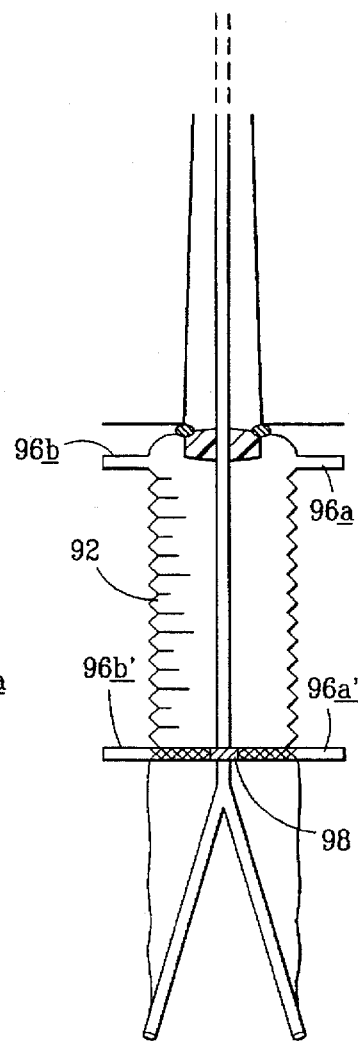

INSTRUMENT, SYSTEM, KIT AND METHOD FOR CATHETERIZATION PROCEDURES

CROSS-REFERENCE TO RELATED APPLICATIONS

This application is related to a co-pending U.S. patent application entitled "Instrument for Catheterization" filed on Jul. 27, 1992 and assigned Ser. No. 07/919,912, which application will issue as U.S. Pat. No. 5,257,979 on Nov. 2, 1993.

TECHNICAL FIELD OF THE INVENTION

The present invention relates to instruments and methods in the health-care industry and, in particular, to a universal instrument for the introduction of a catheter, device or substance into, for the withdrawal of tissue or material from, and for the diagnosis or treatment of any part of a body or body cavity and more particularly, a human body.

DEFINITIONS AND TERMINOLOGY

The following terms used herein shall be defined as:

Universal usage shall mean having one or more of the following capabilities:

may be used anywhere in or on a human body or animal body;

may be used for diagnosis or treatment of disease;

may be used for temporary or permanent devices; and may be used by health-care personnel in many different fields of human and animal health-care.

Discriminatory:

treatment is focused on the diseased part(s) of the body;

Disease:

all altered states of body and mind; and all processes leading to altered states of body and/or mind.

Substance means any matter, including but not limited to:

chemotherapeutic agents;

antibiotics;

genes;

antibodies;

radioactive seeds;

oxygen;

medications;

fluids.

Catheterization means a procedure wherein any tissue, material, structure or substance in a body is entered.

Catheter means a device for insertion into a tissue or material within a body or body cavity, said instrument containing one or more lumens.

Catheterization device:

shall mean any instrument used before, during or after a procedure in order to facilitate catheterization.

Catheterization site:

means any spot or area where a catheter or catheterization device enters or leaves tissue or material.

Comprehensive instrument shall mean either that:

all necessary components are included in the instrument; or all or selected components may be used depending on the catheterization site and depending upon the purpose of catheterization.

Device shall mean any tool, instrument or mechanism which is inserted through the catheterization site including, but not limited to, a catheter or catheterization device, whether pacing leads, monitoring systems, instruments for biopsy, or wires for conduction of heat or cold.

Diagnosis means detection of a condition of a tissue, material, structure or substance of a body, including but not limited to:

angiograms of all types;

obtaining specimens for study (e.g., blood, pleural fluid, tissues, etc.);

obtaining pressure measurements (e.g., Swan Ganz catheter); and insertion of radioactive and other materials.

Treatment means acting upon a tissue, material, structure or substance of a body, including but not limited to:

drainage (e.g., pus, urine, other fluids and substances);

infusion (e.g., fluids, chemicals and other substances); and radioactive seeds and other materials or substances.

Target tissue or material shall mean any tissue or material, conduit containing such tissue or material or conduit connected to such tissue or material wherein said tissue or material is to be accessed.

The present invention:

includes device, instrument, system, kit or methodology described and claimed herein.

Guide-wire shall mean an elongated catheterization device, tool or device for guiding a catheter or other catheterization device, and shall include:

tool or device to allow sampling of tissue or material (e.g., a biopsy forceps);

tool or device to allow treatment of tissue or material (e.g., wire for conduction in hyperthermia or freezing).

"Y" chamber:

a device having a first chamber with an opening for communicating with target tissue or material (as through an interposed needle, dilator, infuser tube or the like) and more than one other chamber communicating with the first chamber.

Hub:

site of attachment of a proximal end of a needle to any other device or connecting system. A hub may form a "Y" chamber.

Distal:

shall mean toward the target tissue or material, i.e., generally away from the operator during a catheterization procedure.

Proximal:

shall mean away from the target tissue or material, i.e., generally toward the operator during a catheterization procedure.

BACKGROUND OF THE INVENTION

In its simplest and earliest form, previously an instrument for catheterization was a tubular object used to drain noxious material (e.g., pus) from the body. The instrument had a distal end, generally sharp, to allow penetration of tissue or of a body structure, a tubular shaft with a lumen, and an open proximal end to allow drainage and introduction of other substances and devices. This instrument has evolved to a plethora of devices (e.g., needles, catheters of different types, cannulae, and biopsy tools, etc.) for catheterization of structures. Each of these has its own specific use(s), method of insertion, problems and complications.

Catheterization of a blood vessel will be used as an illustration. Catheters for blood vessels were initially developed for insertion into peripheral vessels, those which the practitioner could see and/or feel, e.g., on the dorsum of the hand or along the arm. With advances in medicine, it became necessary to catheterize larger blood vessels, many of which were neither visible nor palpable. This required a change in the procedure of catheterization. Several special-purpose catheters and insertion kits (described hereinafter) have become available for the diagnosis and treatment of medical problems and diseases. However, many problems still exist both during and after catheterization. It is one object of this invention to correct many of these problems, examples of which are described below.

There is no catheterization system available which is universal, i.e.:

has a universal procedural method;

can be used to catheterize almost all structures, regardless of the site in/on the body;

can be used for diagnosis and treatment in all parts of the body using the same procedure.

It is a further object of the present invention to be comprehensive, efficient and to fill this void.

The present invention rectifies old problems and eliminates or reduces some of the newer ones (e.g., risk of AIDS by transmission of the HIV virus from patient to practitioner or vice-versa). Moreover, the invention described here can provide a universal system, device and methodology for catheterization procedures. It can be used to provide discriminatory forms of treatment. Such treatments are more efficient and less toxic to the patient because they are focused on the target site. This system requires fewer hospitalizations, is less expensive and more humane. It is more efficient in diagnosis and allows appropriate treatment to be initiated during the same procedure.

For example, prior blood vessel catheterization, and more particularly, catheterization of a subclavian vein in a human body requires the following steps:

1) The skin is cleansed with the solution of choice.

2) The anaesthetic is locally infiltrated.

3) The anatomic landmarks are identified again.

4) The vessel is blindly punctured using a hollow needle with attached syringe.

5) "Flash-back" of blood is observed in the syringe.

6) The syringe is detached from needle so that a guide-wire can be introduced through the hub of the needle.

7) The needle is withdrawn, leaving the guide-wire in place.

8) An incision is made in skin at the site of the guide-wire in the skin.

9) A dilator is introduced over the guide-wire through skin into the blood vessel. This makes a passage in the tissues so that the catheter can subsequently be introduced with ease.

10) The dilator is threaded back out over the guide-wire.

11) A catheter is threaded over the guide-wire into the blood vessel.

12) The guide-wire is removed, leaving the catheter in place.

13) The infusion lines are attached to the ports of the catheter.

14) The catheter is secured to the skin.

15) Dressing is applied. (Dressing changes are done under sterile conditions every 2-3 days depending on the protocol.)

PROBLEMS

Given the state of the art, the following problems can occur during catheterization. These problems have been corrected by the invention herein submitted.

Previously, the practitioner was often required to manipulate the syringe and needle while detaching one from the other. This maneuver can dislodge the needle tip from the lumen of the blood vessel. When this problem occurs, it is necessary to re-attach the syringe to the needle and re-enter the lumen of the blood vessel as evidenced by the "flash-back" of blood into the syringe. Besides being time-consuming and frustrating for both the patient and the practitioner, this problem exposes the patient to the trauma and risks of multiple punctures. One difficulty is that there is no "flash-back" during the insertion of a guide-wire. Hence damage to the blood vessel and/or the adjacent structures with its attendant morbidity and mortality is more frequently observed in such a scenario.

When the syringe is detached from the needle and the proximal end or hub of the needle is open to air, there is a potential risk of air embolism, which may be asymptomatic, but can also be fatal.

These problems continue today. U.S. Pat. Nos. 4,935,008, 4,280,503, 4,655,750, and 4,525,157 have attempted to address the problem of passing a guide-wire without leaving the hub of the needle open to air. They are, however, very limited in that:

only one guide-wire or device can be inserted and the device has only specific applications so that it is not universal "flash-back" cannot be observed none of the problems subsequently discussed are addressed.

Blood flows out of the hub of the needle and there is contact between the patient's blood and practitioner/team members. Although gloves are worn by all members of the team, "breaks" in gloves are well-known. Hence there is no guarantee of protection against the transmission of communicable disease-causing agents (e.g., HIV, hepatitis, etc.). Moreover, guide-wires that are available are of a length that often require the practitioner to feed part of the said wire outward while trying to thread the catheter. Thus, the practitioner is again in contact with potentially infected material. Transmission of a communicable disease is obviously a concern. Use of surgical gloves is routine, but is not a guarantee against contamination. (In the invention herein submitted, at NO time is there contact between any tissue or body fluid of the patient and practitioner. Moreover, no part of the device introduced into the body of a patient is handled directly by the Practitioner.) In the invention herein submitted, the patient and practitioner are protected from being contaminated by each other.

Air embolism can also occur with only a guide-wire in place using the traditional method of catheterization. The present invention rectifies this problem.

Many kits have a guide-wire with a "j" tip. This requires a "feeder" or "straightener" to be attached at the hub of the needle so that the "j" tip is straightened temporarily, thus allowing the guide-wire to be inserted through the needle. This process can be troublesome and the "feeder" becomes unsterile as it falls off the sterile field. In addition, the needle tip can get dislodged from the lumen of the blood vessel. The present invention rectifies the problem.

Another problem frequently encountered during insertion of the guide-wire is that the direction of the bevel or other directional characteristic of the needle is not known. Hence the wire can travel in a direction other than that desired by the practitioner. This results in inappropriate positioning of the guide-wire and consequently, of the catheter. A second catheterization procedure and/or fluoroscopy is then required for the correct placement of the catheter. This requires the use of additional equipment which subjects the patient to radiation and increases the cost of treatment.

The catheter is normally secured to the skin directly (i.e., there is communication between skin tissue and the target tissue or material). In the example of a blood vessel catheterization procedure, the blood stream and the skin are in fluid communication along the exterior surface of the catheter as long as the catheter is in place). The skin is a continuing source of infection, local or systemic, which can lead to many problems resulting in continued hospitalization and even death. U.S. Pat. No. 4,327,723 attempts to combat the problem of infection by the use of a Protective Shield. However, the protective shield does not cover the catheter and introducer entirely so that both still remain in contact with skin. Therefore, the source of infection (i.e., skin to catheter/introducer to bloodstream) is still present and infection continues to be a problem. A catheter is often inserted through the lumen of an introducer. This method has the following potential problems:

Clot can form around the catheter if a side-port is not being used. Clot is a good medium for bacterial growth. Hence there is a likelihood of infection.

Frequently, dextrose-rich fluids are infused through a side-port and bathe the catheter. This also assists bacterial growth. The problem of skin to catheter to bloodstream infection has not been successfully addressed, prior to the present invention, regardless of whether an introducer is used.

Another problem is that multiple physical maneuvers and manipulations and their attendant difficulties and drawbacks are required to achieve catheterization. U.S. Pat. No. 4,995,866 attempts to reduce the number of maneuvers required by combining the needle and a dilator. However, this is "blind instrumentation" and the distal end of the dilator can easily penetrate the back wall of the target vessel resulting in potentially serious problems.

The following problems can occur after catheterization, the correction of which is also an object of the present invention:

1) Local and systemic infections, as described above, can continue to result as long as the catheter is in place and the entry site remains exposed to the skin.

2) Multiple dressing changes are required with currently available catheterization devices. Infection can be introduced into the patient by the practitioner and vice-versa during dressing changes and/or during use of the catheterization device, despite the use of sterile techniques. Infection, in particular, is of grave concern today because:
   a) There is a large number of immune-compromised patients in the patient population.
   b) The cost of medical care in the treatment of infections and resultant problems is significant and soaring.
   c) Results of attempted treatment of infections in this population are still poor.

Another problem is that it is not possible to clean the skin that is in contact with the catheterization device without touching said device and hence damaging the integrity of said device. It is possible to actually introduce infection during dressing changes.

Another problem occurring during dressing changes is that catheters are likely to be inadvertently dislodged from an optimal position. Repositioning and sometimes even the insertion of a new catheter is required. In a critically ill patient, these procedures can be disastrous. U.S. Pat. No. 4,327,723 purports to allow repositioning of the catheter in a sterile environment. However, this is only temporary because the catheter cannot be adequately immobilized in the new position.

Clearly, all these problems contribute to increasing health-care costs.

Several problems that occur during and after catheterization have also been corrected by the present invention.

Infusions of incompatible agents cannot be administered through the same port. U.S. Pat. No. 4,327,723 describes an introducer to be used simultaneously with a pressure-monitoring catheter. This introducer has only one side-port for infusion. Frequently, this side-port is the only avenue for administering medications or fluids while the monitoring catheter (e.g. Swan Ganz) is being positioned. This is clearly a problem because large volumes of fluid need to be administered simultaneously, because some fluids are incompatible with each other and because some fluids need ports designated for their specific use only. Moreover, it is necessary to have a "designated" port, for example, for concomitant hyperalimentation. This generally requires inserting another catheter or converting a "pressure monitoring" line into a port for this use. Neither of these options is optimal. Venous access is limited and one of the most frustrating situations for the practitioner and patient is to have no more access sites available.

Problems pertaining to the diagnosis of disease using catheterization include inability to diagnose (e.g. insufficient tissue for diagnosis; tissue obtained is not from the diseased area). Multiple procedures, including open surgery, are required, the patient is subjected to repeated trauma and risks, and valuable time and money are wasted.

Treatment of many diseases is non-discriminatory (i.e., medications are introduced systemically into the bloodstream so that all parts of the body, whether diseased or not, are exposed to these substances). For example, a large number of agents used in the treatment of cancer are very toxic. The amounts of these medications that are administered are relatively large due to their subsequent dilution in the body. Were these agents administered primarily to target sites, smaller amounts of the therapeutic agents would be required with less toxicity and "healthy" parts of the body would not be damaged.

Furthermore, with prior systems, devices and methods, diagnosis and treatment of diseases (e.g., cancer) is not possible during the same procedure and requires use of a large number of instruments which substantially differ from each other in shape or function.

Discriminatory treatment of diseases is frequently used for lesions on the surface of the body only. Diseases located within a body cavity often require treatment using "open" surgical procedures (e.g., interstitial radiation) and/or systemic medications. Treating the "target" organ without exposing the rest of the body to the toxic side-effects of current agents (e.g., chemotherapy for cancer) is clearly preferable.

This principle has been applied in the past on a limited basis. However, there are still many associated problems.

U.S. Pat. No. 4,192,302 provides a discriminatory method for treatment of liver cancer. A complex shunt is described to isolate the target organ from the rest of the circulation. The shunt treats the blood from the target organ with a chemotherapeutic agent extracorporeally, and then detoxifies the blood before returning it to the general circulation.

This procedure requires hospitalization and a major operation each time treatment is administered. The high cost is clearly a disadvantageous factor, but more importantly, the patient is exposed to repeated morbidity and possible mortality and spends valuable time in the hospital away from the family. U.S. Pat. No. 5,069,662 also describes a discriminatory treatment of liver cancer. The method described is virtually identical to that described in U.S. Pat. No. 4,192,302. The only difference is that catheters are inserted fluoroscopically rather than during an open surgical procedure. Consequently, this procedure also requires multiple hospitalizations and exposes the patient to risks every time the procedure is used (e.g., thrombosis of a vessel, bleeding, damage to the blood vessel such as dissection, etc.).

External radiation has its own well-known complications. Interstitial radiation is used but for lesions within a body cavity, an "open" surgical procedure is necessary. For example, U.S. Pat. No. 4,763,671 addresses local hyperthermia and interstitial radiation. However, an open operation is necessary.

To the best of my knowledge, there is no patent, device or system of catheterization that:

1) deals with the critical problem of transmission of communicable diseases from patient to practitioner or vice-versa;
2) allows diagnosis and treatment of diseases regardless of the site of the disease during the same procedure;
3) is universal;
4) is comprehensive;
5) allows discriminatory treatment of diseases regardless of site of disease and involves minimal, if any, hospitalization followed by subsequent treatments at home;
6) allows repositioning and firm immobilization of a catheter in its new position in a sterile environment without compromising the integrity of said catheter;
7) allows multiple separate ports for infusions while inserting monitoring catheters or other tools through the same access site;
8) corrects important sources of infection;
9) allows the practitioner to know the direction of the bevel of the needle or other directional characteristic or position-sensitive feature at all times;
10) allows the practitioner to observe "flash-back" continuously during maneuvers;
11) allows the insertion of more than one device at the same site without the risk of air embolism;
12) is time and cost-efficient (i.e., the process of catheterization should take less than one minute);
13) has a system of immobilization such that catheters cannot be inadvertently displaced or "pulled out". This problem is significant and, in a critical patient, can mean the difference between life and death.

In summary, there is a clear need for a simple device, system and method of catheterization which is universal, comprehensive and deals with all of the above issues. The various features of the invention submitted in the application achieve various ones of these advantages individually and in combination. The invention also introduces discriminatory treatment for the patient, lowers morbidity and mortality, and allows therapeutic options at low cost.

SUMMARY OF THE INVENTION

The present invention provides for a comprehensive universal instrument and a unified methodology for catheterization to address many of the problems during and after catheterization as already discussed in detail under the BACKGROUND OF THE INVENTION. The instrument includes a needle, syringe or other chamber, "Y" chamber, guide-wire, dilator, sheath, shock sheath, protective sleeve, or combinations thereof, depending on the site and purpose of catheterization. Methods of and devices for immobilization are described. Methodology and instruments for discriminatory treatment of disease using embodiments of said instrument are described. These instruments and methods are universal and introduce safe and easy catheterization using minimally invasive procedures (e.g., laparoscopy and thoracoscopy). The problems or prior systems, devices and methodologies as identified above have been corrected or reduced by the present invention. The instrument substantially corrects problems associated with catheterization and allows safe discriminatory treatment of diseases, e.g., cancer. The instrument(s) and method(s) introduce safe and easy catheterization using minimally invasive procedures, e.g., laparoscopy, thoracoscopy.

Unique aspects, features and/or components of the present invention include the following:

a needle which is suitably marked with indicia to indicate the beveled edge or other directional characteristic or position-sensitive feature of the needle, even when a distal portion of the needle is not visible to the practitioner;

a needle having one or more lumina to allow the simultaneous insertion or withdrawal of substances or devices at the same puncture site;

a "Y" chamber which allows the practitioner to observe "flash-back" in a syringe or other viewable chamber while allowing the introduction or removal of a guide-wire, catheter, radiation seeds, biopsy instrument, tools, systems, medicines or other devices or substances;

a syringe or chamber which allows the practitioner to observe "flash-back", and to withdraw and to infuse substances;

a guide-wire of sufficient length so that the practitioner does not come into contact with any part of the wire that has already been in the catheterized system (e.g., bloodstream). Often the practitioner inserts the guide-wire into the system and then moves it "out" before threading the catheter, thus "touching" potentially contaminated wire;

a dilator which is incorporated over a needle to allow dilation of tissues for easy insertion of subsequent devices, and particularly devices used in a catheterization procedure. This dilator may be progressively tapered so that dilation occurs in a progressive manner. In one embodiment, the dilator has a wall with a lumen, which can be inflated to allow dilation at the discretion of the practitioner. The dilator has tabs for easy maneuverability. In a further preferred embodiment, a dilator is provided with a valve, self-sealing plug, grommet or other sealing device;

a sheath is preferably incorporated over a dilator. The sheath is substantially shorter than the dilator and has tabs to allow ease of movement and subsequent securing of the sheath to the skin. In a preferred embodiment of a combination catheterization instrument, the sheath does not communicate with the target catheterized tissue or material; but, rather serves as a shield between the skin and the target tissue and any catheter system;

An alternative sheath has a self-sealing plug, grommet, or other sealing device which prevents unwanted flow of substances therethrough and which may also incorporate a bactericidal agent;

a "shock" sheath is uniquely provided with multiple lumens or ports separated from each other to allow one or more catheterization devices to pass therethrough while sealingly allowing other lumens to communicate to and from the target tissue or material without interfering with the other catheterization device or devices. The "shock" sheath is advantageous especially in emergency situations where multiple ports may be required immediately for the reasons described in the BACKGROUND OF THE INVENTION;

a protective sleeve which is preferably pre-assembled on a catheter or device used for catheterization, but which in an alternative embodiment may be secured around the catheter or device used for catheterization after such device is inserted into the target tissue or material. This is not the mode of construction today and practitioners are familiar with the frustrating situation where they have omitted the step of its assembly. The protective sleeve preferably incorporates the entire catheter, including the port limbs and the sheath, leaving only the tabs of the sheath exposed to allow fixation (i.e., immobilization). The protective sleeve may be in one or two sections and allows repositioning and firm immobilization of the catheter in different positions while maintaining sterility at all times. The protective sleeve is easily modified for use over a guide-wire or other catheterization device or tool. The catheter is protected at all times. Hence, contamination and catheter damage should be virtually eliminated.

BRIEF DESCRIPTION OF THE DRAWINGS

For a more complete understanding of the present invention and for further advantages thereof, reference is now made to the following DESCRIPTION OF THE PREFERRED EMBODIMENTS taken in conjunction with the accompanying claims and drawings in which:

FIG. 1 is a perspective view of one embodiment of the present instrument;

FIG. 2 is a sectional view taken generally along sectional lines 2—2 of FIG. 1;

FIG. 2a is a schematic sectional view through the central axis of an alternative tapered needle and tapered dilator according to the invention.

FIG. 3 is a sectional view taken generally along sectional lines 3—3 of FIG. 2;

FIG. 8 is a partial section view depicting an alternative embodiment of an instrument similar to that shown in FIG. 5 wherein the catheter has a plurality of prongs;

FIG. 9 is an enlarged partial plan view of another embodiment of catheterization instrument wherein a plurality of prongs of the catheter have side-holes;

FIG. 10a is a perspective view of the protective sleeve of the present invention;

FIG. 10b is a perspective view of the protective sleeve in a collapsed position;

FIG. 10c is a perspective view of the protective sleeve in an extended position with its adjustable length bridge;

DETAILED DESCRIPTION OF THE PREFERRED EMBODIMENTS

Figure 4:
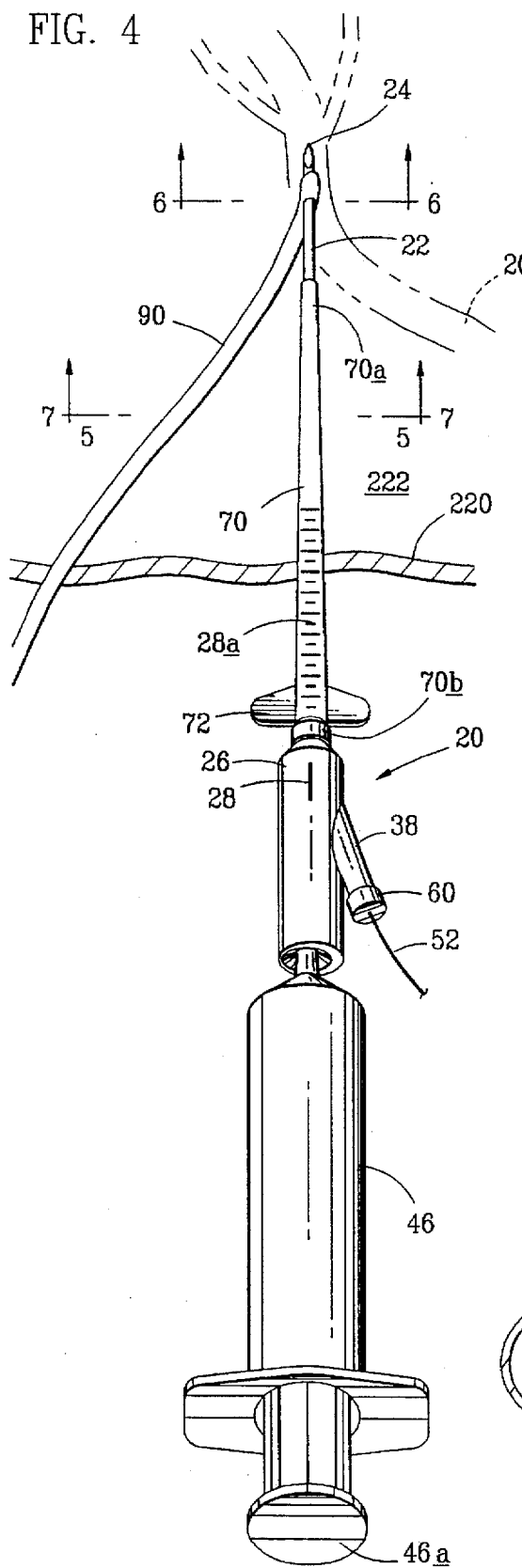
FIG. 4 is a perspective view of another preferred embodiment of the present invention incorporating a catheter on a needle, wherein said embodiment is particularly recommended for use with minimally invasive procedures and also for discriminatory treatment of disease.

The embodiments presented are for illustrative purposes only and do not, in any way, limit the scope of the invention. In particular, anyone skilled in the art can make numerous modifications using the proposed instrument, system, and methodology.

Referring simultaneously to FIGS. 1, 2, 3 and 4, the present catheterization instrument is illustrated, and is generally identified by the numeral 20. Instrument 20 includes a needle 22 having a distal end 22a and a proximal or rear end 22b. Needle 22 can be constructed, for example, of stainless steel or similar material and includes a sharpened (preferably beveled) side 24 of needle end 22a. End 22b of needle 22 is interconnected to a hub 26. As illustrated in FIG. 1, hub 26 includes indicia 28 to indicate a position of a directional characteristic such as the direction of beveled side 24 or other position-sensitive feature of needle 22. Indicia 28 assists the practitioner in locating the position of beveled side 24 or the directional or position-sensitive characteristic of needle 22, while needle 22 is inserted into a target tissue or material, such as a blood vessel, which is not visible to or palpable by the practitioner (e.g., subclavian vein—a large blood vessel located under the collarbone in the chest).

Needle 22 in the embodiment shown in FIGS. 1–4 includes a first longitudinal bore or lumen 30 and a second longitudinal bore or lumen 32. Although lumens 30 and 32 are illustrated in FIG. 2, it will be understood that the present invention can be utilized with any number of lumens (including one) depending upon the number of guide-wires, tools, devices or substances to be inserted through the needle at a single puncture site. First lumen 30 and second lumen 32 originate at beveled side 24 in a parallel relationship, with first lumen 30 and second lumen 32 being separated from each other by an interior wall 34 of needle 22. Lumens 30 and 32 are of sufficient internal diameter to allow passage of guide-wires, or other devices or substances used in various procedures in the health-care field.

Lumen 30 is preferably the same cross-sectional shape, for example, rectilinear, along the entire length of needle 22 and has its terminus 30a at hub 26 of needle 22. Lumen 32 is also preferably the same cross-sectional shape, for example, rectilinear, along the substantial longitudinal length of needle 22, with its terminus 32a diverging at an angle from first lumen 30 at hub 26 thereby forming a side arm 38 of needle 22. Hub 26 thereby physically connects the lumens at a Y chamber 27. Hub 26 may itself be a part of "Y" chamber 27 as in FIG. 4, or as in FIGS. 1 and 2, "Y" chamber 27 may be detachably connected to any hub 26 of any needle 22.

Where it is desired to use several lumens (i.e., more than two) with the needle 22, additional side arms can be utilized in a "Y" chamber connected to a hub similar to hub 26 such that additional guide-wires or tools can be inserted through needle 22.

Hub 26 in a preferred embodiment is constructed of plastic or similar material. Hub 26 is concentrically attached to needle 22 at end 22b and in a manner known and used for the attachment of hub casings of single lumen needles. "Y" chamber 27 includes an internal bore 40 which is contiguously aligned with first lumen 30. Side arm 38 includes an internal bore 42 which is contiguously aligned with second lumen 32. Preferably, a portion of the material of "Y" chamber 27 is transparent adjacent internal bores 40 and 42 so that the content of internal bores 40 and 42 can be observed.

Bore 40 of "Y" chamber 27 increases in diameter at bore expansion 44, such that end 40a of bore 40 is adapted to removably engage a syringe barrel or other reversibly aspiratable chamber 46. Preferably, syringe barrel 46 has a piston 46a and is connectable to hub 26, as through "Y" chamber 27 for example, by using the inverted frusto-conically shaped aperture 48. Normally, syringe or chamber 46 is used to observe "flash-back" and for withdrawal, aspiration and introduction of substances to the catheterized site through lumen 30. Syringe or chamber 46 is always in communication with lumen 30 so that there is an uninterrupted communication with the catheterized site. Similarly, bore 42 terminates in an inverted frusto-conically shaped aperture 50 formed in side arm 38 to facilitate the insertion of a guide-wire 52 into bore 42 and second lumen 32 of needle 22.

Bore 42 of side arm 38 is engaged by a valve, grommet or other sealing device 60, which can be constructed of rubber or similar material, and is retained by locking bead 62 of hub 26. Valve, grommet or sealing device 60 is adapted to be pierced and penetrated by guide-wire 52 (other instrument, tool or device) thereby allowing insertion of guide-wire 52 through valve, grommet or self-sealing device 60 and into bore 42 of second lumen 32 which self-sealing grommet prohibits the entry of air into or escape of substances from the catheterized site punctured by beveled end 24 of needle 22.

A self-sealing device 31 may be interposed within the hollow elongated shaft 30 or lumen 30 of needle 22 for restricting movement of substances in at least one longitudinal direction through the hollow elongated shaft 30.

An important aspect of the present instrument 20 is the use of a dilator 70 having ends 70a and 70b. Dilator 70 is tapered at end 70a to approximately the diameter of end 22a of needle 22 and gradually increases in diameter throughout its length to end 70b. Tapering allows a gradual transition in size to accomplish progressive dilation of the opening in the blood vessel (synonymous with any catheterized site in this presentation) and adjacent tissues with subsequent easy insertion of the catheter.

It is recommended that end 70b of dilator 70 include wings or tabs 72 to allow easy maneuverability of dilator 70 along the guide-wire 52 and along the needle 22 (this latter may be moved out of position depending on the preference of the practitioner). Any standard design for wings or tabs can be used. Dilator 70 fits snugly over needle 22 to ensure that there is no trauma to tissue or material as a result of a sudden transition in size.

In a preferred embodiment, dilator 70 terminates at end 70a approximately 0.5 to 1.5 cm. from end 22a of needle 22. It is understood that, in general, both the design and length of the dilator can be varied.

FIG. 2a depicts an alternative embodiment of an instrument for facilitating catheterization including a needle 23 having a smoothly tapered surface with a distal portion 23a smaller than a proximal portion 23b; and a dilator 71 having an exterior diameter increasing from a distal portion 71a to a proximal portion 71b circumferentially disposed around the needle 23 for expanding tissue or material punctured by the needle so that catheterization is facilitated. Also depicted is a self-sealing device 33 interposed within an elongated lumen 73 formed in dilator 71, for restricting movement of substances in at least one longitudinal direction therethrough.

Figure 14:
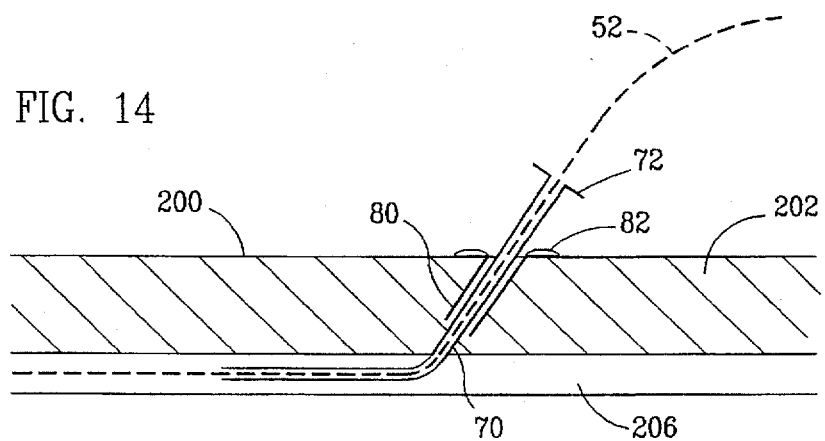
FIG. 14 is a side view of one embodiment of the invention showing a guide-wire, dilator and sheath in place so that the sheath is secured to the skin and does not communicate with the target tissue (i.e., the blood vessel in the case shown.)

An important feature of the present invention is the use of a sheath 80 having ends 80a and 80b. Sheath 80 is circumferentially disposed around dilator 70 and extends from end 70b of dilator 70 to a position between ends 70a and 70b of dilator 70. One embodiment includes wings 82. Other embodiments such as tabs, or other projecting structures allowing grasping and maneuvering of the sheath or through which sutures are passed, can also be used to immobilize the sheath, as by affixing it to the skin 200. It will be noted with reference to FIGS. 14 and 15 below that, unlike dilator 70, sheath 80 makes no contact whatever with the target tissue or material at the catheterized site (e.g., bloodstream 206). The sheath 80 facilitates correcting two major problems encountered during and after catheterization: infection and air embolism. Infection is virtually eliminated because the sheath 80 is not in direct contact with the bloodstream 206 and the catheter 90, inserted through the sheath 80 into the bloodstream 206, is not in contact with skin 200 at any time. As shown in FIGS. 10a and 10b, sheath 80 preferably has a valve, grommet or other self-sealing device 86 which prevents air embolism while the guide-wires, catheters or other devices are inserted, withdrawn or held in place during the process of catheterization. Moreover, leaving the sheath 80 in place after removal of a catheter 90 allows the portion of tract from bloodstream 206 to subcutaneous tissue 202 to heal. Thus, when the sheath 80 is removed, the only remaining tract extends from skin 200 to subcutaneous tissue 202. Hence, the potential for air embolism is virtually eliminated.

Referring now to FIGS. 10a and 10b, another important component of the submitted invention is a protective sleeve 92 which may be preassembled with a catheter 90. The sheath 80 and its parts as already described includes a valve, grommet or self-sealing device 86 through which a catheter 90 is passed. The catheter has a distal end 90a and two ports 90b and 90c. The protective sleeve 92 is, in this instance, made of a synthetic soft material capable of being "accordioned." This sleeve 92 fits circumferentially over the sheath 80 just distal to the tabs 82 of sheath 80 using any sealing mechanism known in the industry (e.g., an "O" ring at location 94a). It is recommended that the space between tabs 82 and location 94a be the least amount consistent with known manufacturing techniques. Protective sleeve 92 is bonded distally to the ends of the catheter ports 90b and 90c at points 94b and 94c leaving only the actual ports (i.e., access sites) exposed. These ports are kept capped and sterile using well-known methods. The protective sleeve 92 covers the entire system outside the patient's skin 200 with the exception of the tabs 82 for fixation of sheath 80. As discussed earlier, these tabs 82 and sheath 80 are not in communication with the catheterized target tissue or material, such as at area 206 and cannot become a source of infection of the target tissue or material.

Figure 10D:
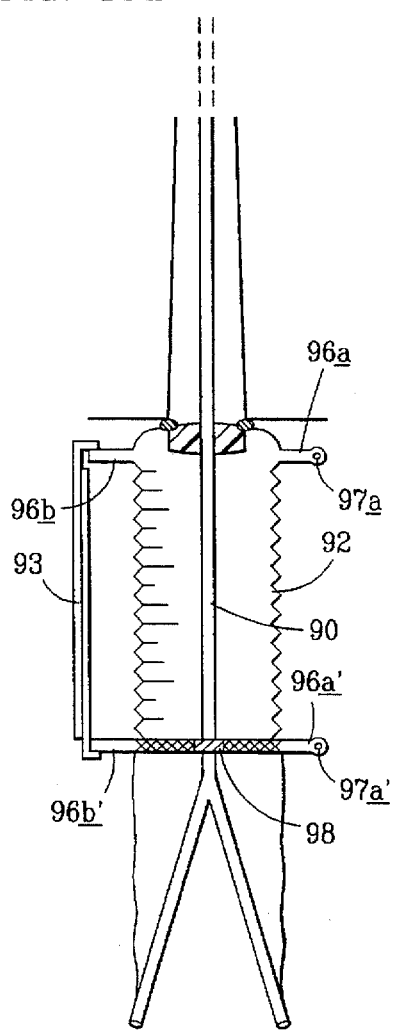
FIG. 10d is a perspective view of the protective sleeve with its adjustable length bridge in a collapsed position.

Another novel feature of this invention is the use of multiple tabs. Tabs 96a and 96b on protective sleeve 92 are situated distally (i.e., toward sheath 80). Tabs 96a' and 96b' are located proximally on protective sleeve 92 (i.e., nearer the entry ports 90b and 90c of catheter 90). Several embodiments can be used. For example, as shown in FIGS. 10c and 10d, each tab may have an "eye" 97a and 97a' allowing the passage of a suture to approximate the "accordioned" length of the protective sleeve 92. The skin to which the eyes 97a and 97a' are secured, in combination with applied sutures can serve as an adjustable length bridge therebetween. Alternatively, a mechanical bridge structure 93 may be used for adjusting the length of sleeve 92 and maintaining a desired length. Thus, tab 96b is attached to tab 96b' using bridge 93 which is a bridge whose length can be varied selectively. Tab 96a can be attached to tab 96a' using an identical device or both eyes 97 and a bridge 93 might be provided on opposite sides to allow the medical professional to choose which device to use. Alternative mechanisms of attachment might also be used, such as a clip of adjustable length.

FIG. 10d shows the protective sleeve 92 "accordioned" or adjusted to a shorter length as catheter 90 is maneuvered further into the body. The catheter 90 has been repositioned and immobilized in its new position, maintaining complete sterility in the process. As shown, tab 96a is now closer to tab 96a' and tab 96b is closer to tab 96b'. Another feature that can be easily added is the bonding, or attaching by any other means, of the protective sleeve 92 to the catheter 90 at site 98. To illustrate further, when the catheter is used in a body cavity, there is the possibility of the catheter getting kinked. In such a situation, the material of the protective sleeve 92 can be such that the practitioner can mold the form or shape of protective sleeve 92 and decide exactly how he or she wishes the catheter to lie.

Figure 13:
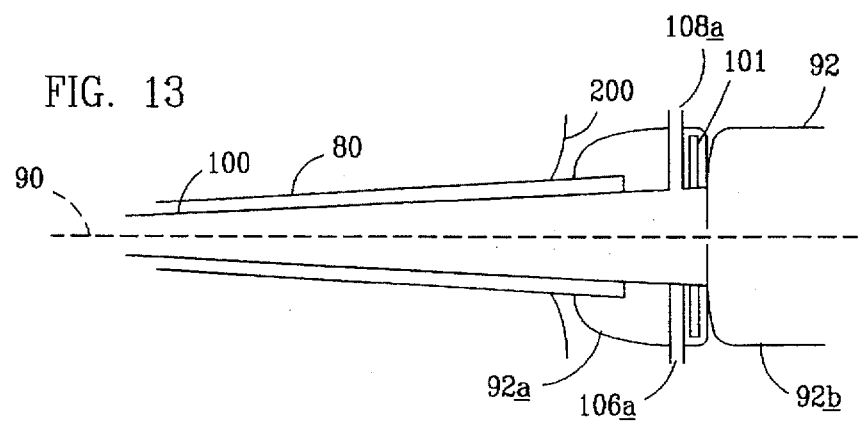
FIG. 13 is a side view of an adaptation of the protective sleeve for use with a "shock" sheath and a catheter simultaneously.

It is possible to make this protective sleeve 92 in two parts such that one half is already attached to the sheath 80. This is shown in FIG. 13. Protective sleeve 92a at least partially encompasses shock sheath 100, which serves to communicate with target tissue while a sheath 90 specifically shields the skin from communicating with the target tissue. Shock sheath 100 may also include side-ports 106a and 108a which sealingly project partially through protective sleeve 92a. Protective sleeve 92b covers the catheter 90. However, I believe that the protective sleeve 92 as described earlier is easier for the practitioner to use.

Figure 11:
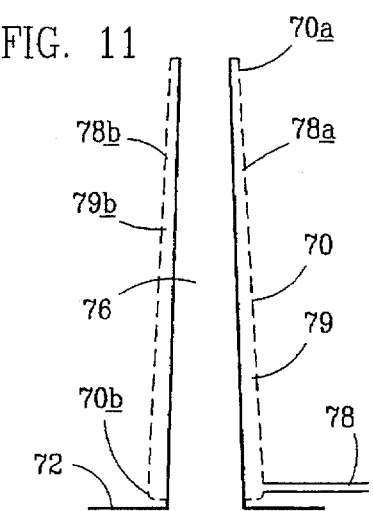
FIG. 11 is an enlarged view of another embodiment of the dilator shown in FIGS. 1 or 4.

Another preferred embodiment of a dilator 70 is shown in FIG. 11. The dilator 70 has a distal end 70a and a proximal end 70b. Dilator 70 includes a lumen 76. There is a side-port 78 which communicates with lumen 78a, which is situated along and outside lumen 76. A flexible wall 79a exterior to lumen 78a may be dilated with air, water or other substance to an extent determined by the practitioner. Lumen 78a will preferably extend circumferentially around and along the outside of lumen 76 as at 78b so that an entire circumferential wall 79b can be expanded in diameter through inflation. It is suggested that such an expansion or dilation maneuver be performed after the needle 22 has been optimally situated and a guide-wire inserted. This ensures dilation of tissues only when the practitioner is sure that he or she is ready to insert the catheter or tool. In addition, the practitioner can use the same system without regard to the size of the instrument to be inserted.

Figure 12:
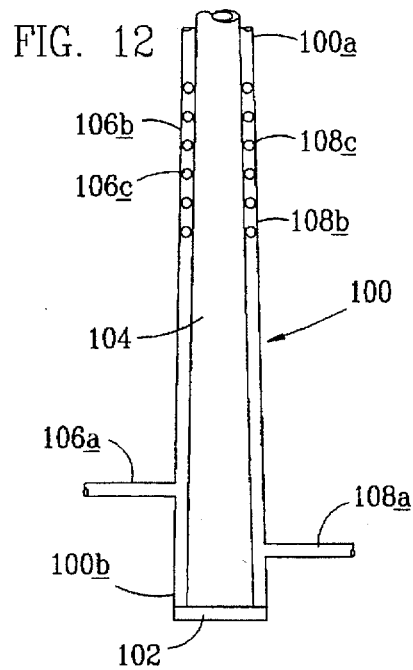
FIG. 12 is a sectional view of the "shock" sheath of the present invention.

Yet another important component of the invention is a "shock sheath" 100. FIG. 12 is a sectional view of a "shock sheath" 100 and shows a distal end 100a and a proximal end 100b. A valve, grommet or other self-sealing device 102 is shown through which a tool (e.g., Swan Ganz catheter) may be passed into an isolated lumen 104 of shock sheath 100. A side-port 106a preferably communicates only with its own separate lumen 106b. This lumen 106b may have one or more distal holes 106c and preferably has multiple side holes 106c on the outside wall distally to allow the infusions of large volumes of fluids. Similarly, there is another side-port 108a which communicates with lumen 108b. Preferably, the lumen 108b is not in communication with any other lumen and has multiple holes 108c situated distally. The separateness helps to eliminate the possibility of any cross-contamination from the contents of one lumen to the other. Note that FIG. 12 is only illustrative. If desired, any number of such side-ports and lumens may be incorporated. The lumens may be situated longitudinally or circumferentially to each other. When the shock sheath 100 is used, the protective sleeve 92 used will preferably have two parts, 92a and 92b, so that the shock sheath 100 and the catheter 90 are protected against cross-contamination also. This device will function according to the principles already described under the description of protective sleeve 92.

FIG. 13 illustrates the use of protective sleeve 92, sheath 80, and shock sheath 100. The shock sheath 100 may have tabs 101 which are easily incorporated on the proximal end (i.e., the side towards the practitioner). Antiseptic, bactericidal and other agents may be used to coat or be incorporated into either part of the system or the whole system.

Procedure for Catheterization

Referring to FIGS. 1, 2 13, and 14, a catheterization procedure using the inventive devices, systems, and methods may be more fully understood. The practitioner positions the needle 22 such that the indicia 28 allow him or her to determine the direction in which the guide-wire 52 exits the needle tip 22a. This feature is important because it allows the practitioner to determine the initial course the guide-wire 52 will take in the lumen of the vessel 206 (e.g., the subclavian vein) and dictates the direction of the catheter. Guide-wire 52 pierces valve, grommet or sealing device 60 and passes into hub 26, which hub 26 may be a "Y" chamber 27. The wire exits the needle tip 22a by passing through bore 42 into lumen 32. The practitioner can observe flash-back in "Y" chamber 27 or preferably syringe 46 or another transparent chamber 46 throughout this procedure.

The instrument is moved out proximally so that the guide-wire is left in the lumen of the blood vessel and the needle tip removed from the lumen of said blood vessel, thus substantially eliminating the risk of damage to the blood vessel by inadvertent needle motion.

The dilator 70 and sheath 80 are maneuvered simultaneously along the guide-wire 52, which guide-wire extends into blood vessel lumen 206. Dilator 70 is pushed into vessel 206 and sheath 80 is maneuvered below the skin to a position short of the target catheterization tissue 206. The needle 22 with the attached syringe 46 is removed from the puncture site. Tabs 82 of sheath 80 are secured to the skin 200, as by suturing (shown in FIG. 14), or with another securing mechanism as will be described below with reference to FIGS. 23 and 25.

The dilator 70 is removed and a catheter 90, or other catheterization device, preferably with the protective sleeve 92 therearound is "threaded" over the guide-wire 52 into the target tissue or material 206. The protective sleeve 92 is secured to sheath 80 at 94a as shown in FIG. 10a. Tab 96a of protective sleeve 92 is attached to tab 96a' and tab 96b to tab 96b' at a desired adjusted length. A small dressing may be applied or a little tincture benzoin sprayed around the skin puncture area. This methodology provides a comprehensive, safe, and efficient system. For instance, subclavian vein catheterization using this procedure should take less than one minute to perform after the proper site of catheterization is determined as by observing "flash-back." Further care of the catheter and catheterization site is safe with the risk of inadvertent "pulling out" of the catheter substantially decreased due to the system of immobilization. The site is also infection-free because sheaths and protective sleeves shield the target tissue and the catheter or other catheterization device from contact with the ski from "touching" during subsequent handling. It is now possible to cleanse the skin adjacent and immediately around the catheterization site without the danger of the catheter coming into contact with cleansing agents, which agents often damage the catheter. The procedure is economical because it is quickly accomplished with a comprehensive device or kit.

Definitive diagnosis of many diseases is obtained by performing a biopsy on target tissue or materials. Often the practitioner obtains a sample from the target tissue in two steps. The practitioner first aspirates the site to be sure it is the target tissue and not a blood vessel in this case. Once this is ascertained, the lesion is biopsied. Using instrument 20, the target tissue or material, such as at a lesion is entered with the needle 22 and syringe or chamber 46 is used for observing "flash-back." If no blood is observed, a biopsy forceps is introduced through the side arm 38 of the "Y" chamber 27 (as was guide-wire 52 above) and a sample of tissue is obtained and withdrawn with the biopsy forceps. There are many different catheterization devices, such as a variety of biopsy instruments available to choose from. Certainly, it is easy for one skilled in the field to modify an existing biopsy forceps or other catheterization device to fit into instrument 20.

Figure 17:
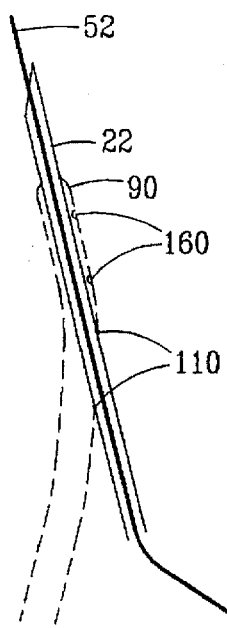
FIG. 17 is a partial side view of a preferred embodiment of the present invention recommended particularly for use endoscopically and also for discriminatory treatment.

The discriminatory treatment of diseases means treatment in which the agent for treatment is administered either into a conduit situated close to the diseased tissue part or organ, and/or directly into the diseased tissue. For example, an intracavitary cancer in the abdomen or chest may be the target tissue for discriminatory treatment. Surgical instrument 20 can be used without open surgery, i.e., with minimally invasive procedures, to catheterize a specific blood vessel entering the cancerous organ or even a particular blood vessel entering the specific part of the organ with cancer. FIG. 17 shows one preferred embodiment of the invention. Needle 22 is used to puncture the blood vessel and "flash-back" is ascertained using the syringe or chamber 46 as before. Guide-wire 52 is inserted into the lumen of the blood vessel, needle 22 may be withdrawn from said blood vessel, and the catheter 90 is threaded immediately into the lumen of the blood vessel. The "Y" chamber 27 and syringe or chamber 46 which are used as described above are not depicted in FIG. 17 for clarity. A catheter 90 which preferably has side holes 160 is preferably placed over the needle 22 at the start of the procedure by which the catheter is inserted into the cancerous target tissue or material. This preliminary step is accomplished by inserting needle 22 through an aperture 110 on the side wall of the catheter, which aperture 110 preferably includes a valve, grommet or sealing device 111. Aperture 110 may also be a functional side hole of the catheter after it is in place. It is recommended that the aperture 110 be located close to the distal tip of the catheter. This embodiment is particularly recommended for use endoscopically (e.g., laparoscopically). In this application, the catheter may be attached to a subcutaneous port of a type which may be available and through which therapeutic agents may be instilled in the port as desired without any need for subsequent hospitalizations for surgical procedures.

In a preferred embodiment for discriminatory treatment, it is advantageous to use dilator 70 to push the catheter off needle 22 so that the catheter remains in the target tissue after withdrawing needle 22, as will be discussed below in referring to FIGS. 4 and 5. This procedure requires minimal, if any, hospitalization, is safe, efficient, discriminatory, and allows treatment at home.

Figure 18:
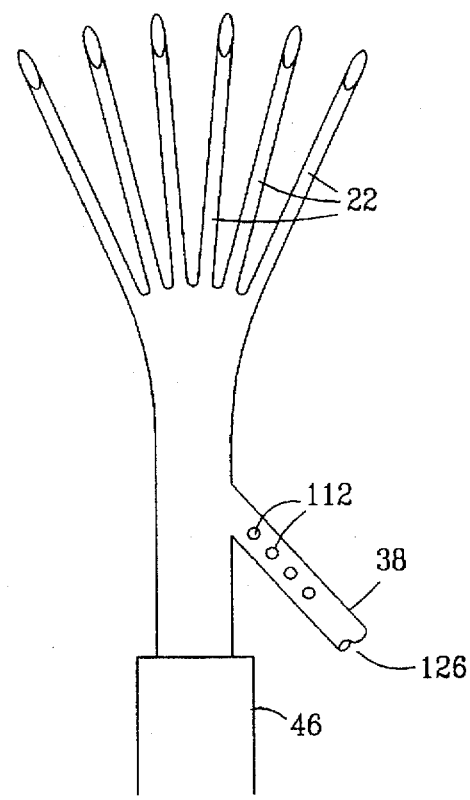
FIG. 18 is a partial sectional view of yet another embodiment of the invention that can be used for chemotherapy or the insertion of radioactive seeds or other substances.

FIG. 18 illustrates the use of an alternative embodiment of instrument 20 in providing discriminatory treatment by inserting the therapeutic agent directly into the target tissue or material such as a cancerous lesion, rather than through blood vessel circulation of the therapeutic agent. The lesion or other tissue or material is punctured with the needle 22, lack of "flash-back" is observed in syringe or chamber 46. Radiation seeds 112 are inserted through the "Y" chamber 27 in lieu of guide-wire 52 for identification of proper target tissue. This procedure may be repeated at different sites on and in the tumor. The location and particularly the depth of the needle 22 is a position-sensitive feature. It is an aspect of the invention that the needle 22 have indicia marked, as with graduation marks, along its length and particularly along a proximal portion so that the practitioner may observe the depth of the needle 22. This information together with known dimension of the target tissue or material makes the procedure safe and efficient. Typically, varying the depth at different sites within the tumor mass is advantageous for complete treatment. The insertion of the radiation seeds 112 can be accomplished in several ways and includes (a) maneuvering them along the lumen 32a with a wire or other instrument or (b) using an ejection gun at 126 to displace the seeds through the "Y" chamber and needle. If the latter is the preferred method, this invention may be used with multiple needles 22 as shown in FIG. 18.

Figure 19:
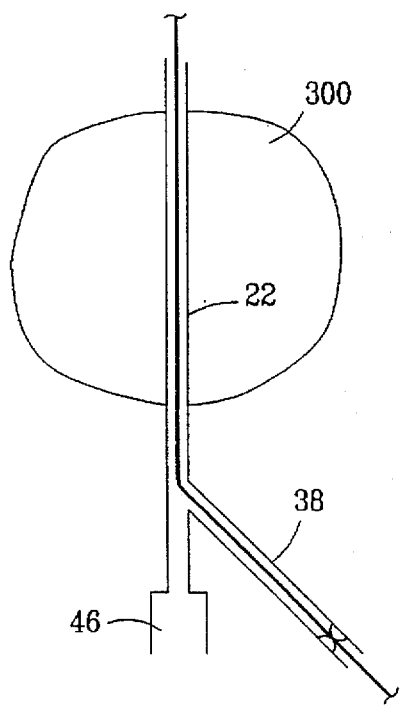
FIG. 19 is a schematic partial sectional view of an embodiment of the invention that can be used for the insertion of a catheter containing radioactive seeds or a catheter for administering substances (e.g., chemotherapy and antibiotics)
Figure 20:
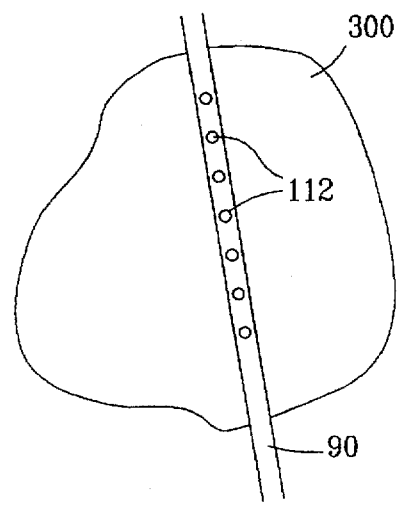
FIG. 20 is a sectional view of the catheter of FIG. 19 in place and extending the entire depth of the tumor. Note that any number of such catheters may be inserted in different planes through the tumor mass.

Referring to FIGS. 19 and 20, if the practitioner desires to insert a catheter containing radioactive seeds 112 into a tumor 300, this is easily done using this invention by following the steps outlined above. Instead of guide-wire 52, a catheter containing radioactive seeds 112 is inserted. Once again, several catheters can be inserted separately or simultaneously.

Figure 5:
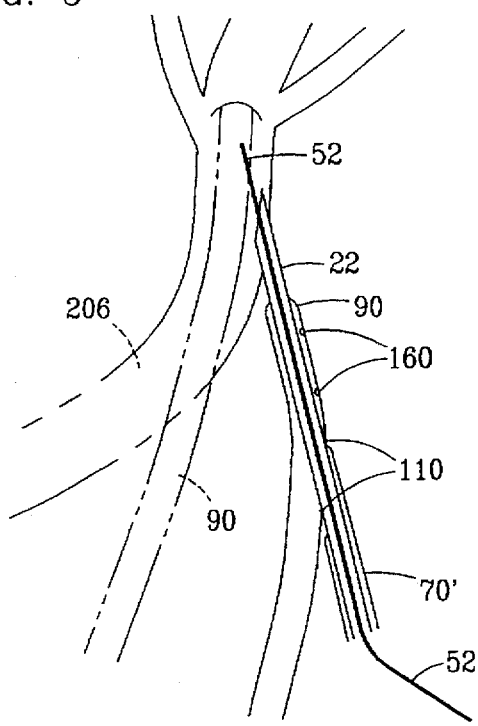
FIG. 5 is a partial sectional view taken parallel to the needle axis generally along sectional lines 5—5 of a part of the instrument depicted in FIG. 4, comprising a needle, guide-wire, dilator and catheter (shown in phantom lines)
Figure 6:
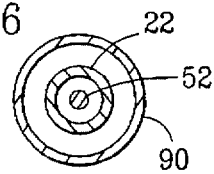
FIG. 6 is an enlarged sectional view taken generally along sectional lines 6—6 of the instrument depicted in FIG. 4.
Figure 7:
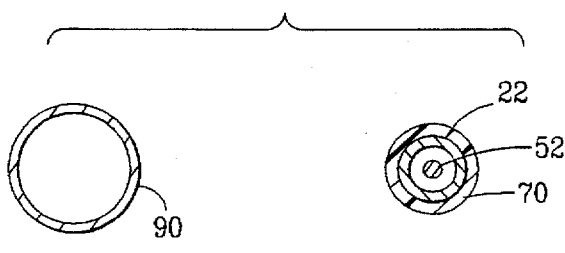
FIG. 7 is a sectional view taken perpendicular to the needle axis generally along sectional lines 7—7 of the instrument depicted in FIG. 4.

FIG. 4 shows an alternative embodiment of an instrument 20, wherein a catheter 90 is circumferentially disposed around a needle 22 and in place of dilator 70, a substantially tubular member 70' is used as a "pusher." Hence, the term "pusher member." FIG. 5 shows a sectional view of the part of the instrument wherein the catheter is incorporated on the needle. FIG. 6 is a sectional view of that part of the instrument in FIG. 4 taken along section lines 6—6 wherein the catheter is incorporated on the needle. FIG. 7 is a sectional view of that part of the instrument in FIG. 4 taken along section lines 7—7 wherein the pusher member is incorporated on the needle and the catheter is seen adjacent to this part of the instrument. This alternative preferred embodiment is particularly advantageous for catheterization performed using minimally invasive procedures such as laparoscopy and thoracoscopy, where it is understood that the components of the invention are of sufficient lengths for insertion into a particular body cavity, organ, other structure or material.

For illustrative purposes, consider catheterizing a blood vessel (e.g., the hepatic artery) located within the abdominal cavity. This catheterization can be accomplished in two ways using current methods:

using an open surgical procedure to visualize and catheterize the blood vessel, or catheterizing the said vessel by entering the arterial system at a distant point (e.g., femoral artery) and then threading the catheter into the blood vessel with the help of various guiding systems, including, for example, fluoroscopy.

(See BACKGROUND OF THE INVENTION for a detailed discussion of the associated problems.)

Using the instrument depicted in FIG. 4, the practitioner can now safely, easily and quickly catheterize the blood vessel using laparoscopy or other minimally invasive procedures to observe the blood vessel, as on a television monitor or using fiber-optical means. The suggested procedure is:

locate the blood vessel 206;

penetrate the body wall 220 with needle 22 and pusher member 70';

puncture the wall of the blood vessel 206;

observe flashback in the syringe or chamber 46;

use the indica 28 to determine the direction of the guide-wire 52;

introduce the guide-wire 52 into the blood vessel 206 through the side arm and grommet 60 of the "Y" chamber 27;

draw back the instrument 20 so that the needle 22 exits the blood vessel 206, leaving the guide-wire 52 in place within the vessel lumen 206;

use the pusher member 70' as "pusher" to slide the catheter 90 off the needle 22;

slide the catheter 90 along the guide-wire 52 into the blood vessel lumen 206;

remove the instrument 20, leaving the catheter 90 in place.

Note that in some situations, the ease, safety or speed of said procedure can be enhanced using a curved needle, depending on the site to be catheterized.

FIG. 8 shows another embodiment of the instrument of FIG. 4 or 5 wherein a catheter 90a has multiple limbs or prongs 91a, b and c having side holes 160. Prongs 91 provide the important benefit of allowing the practitioner to insert substances simultaneously into different parts of tissue or material. This feature is of particular importance in the treatment of solid tissues. Further, this embodiment of instrument 20 uniquely and advantageously permits discriminatory or focused treatment of diseases, such as cancer.

FIG. 9 shows an embodiment of the instrument of FIG. 8 where the prongs 91 of catheter 90a have multiple side holes 160, and where prongs 91 are embedded in tumor 300. The side holes 160 allow the practitioner to insert substances (e.g., chemotherapeutic agents) into multiple sites within said tumor.

The features of the instruments of FIGS. 8 and 9 are of particular importance because:

it is difficult for substances to diffuse through solid structures (e.g., tumors), and the pressure within tumor cells is often substantially higher than the pressure in surrounding tissues, hence precluding or substantially diminishing the efficient delivery of substances (e.g., chemotherapeutic agents) through the blood stream.

Improvements in the performance of the embodiments of instruments 20 of FIGS. 8 and 9 can be achieved by making tips 93 of the prongs 91 of rigid material, and making the tips 93 sharp to allow easier penetration of solid tissues. Further improvements in the performance of the instruments shown in FIGS. 4, 8 and 9 can be made by including indicia 28a on said instruments to allow the practitioner to determine the depth to which the tissue has been penetrated.

Figure 10F:
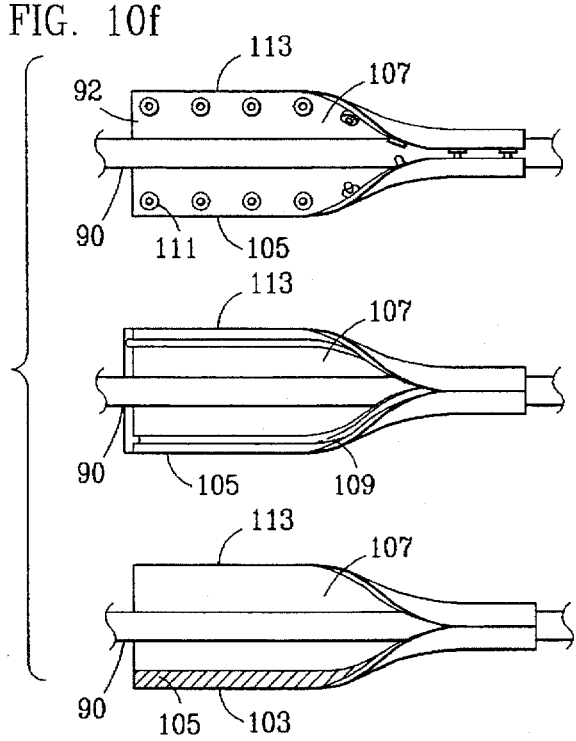
FIG. 10f is a sectional view of another embodiment of the protective sleeve.
Figure 10E:
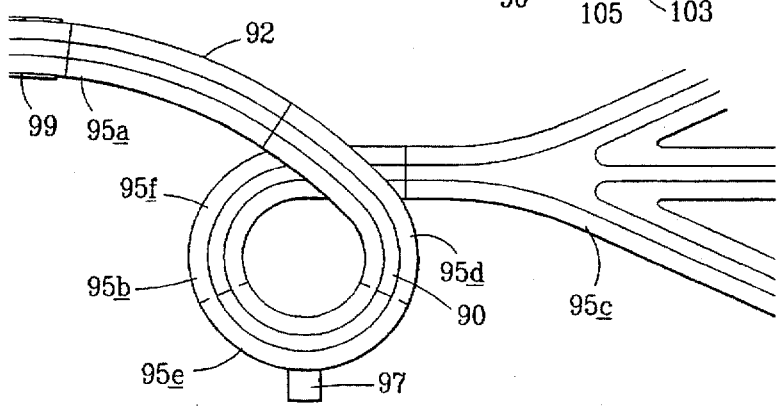
FIG. 10e is a sectional view of a preferred embodiment of the protective sleeve of the present invention wherein a coiled section is included.

FIG. 10e shows a part of an alternative embodiment of a protective sleeve 92 wherein protective sleeve 92 encompasses or partially encompasses a catheter 90. Protective sleeve 92 advantageously has three sections:

a distal section 95a which is located closer to the catheterization site;

a proximal section 95c which is located away from the catheterization site; and a middle section 95b which is located between distal section 95a and proximal section 95c;

Middle section 95b may be advantageously coiled and may preferably include one or more tabs 97 or other means for attaching the protective sleeve 92 to the skin 200. Middle section 95b can be made of a material having sufficient firmness to maintain a predetermined length or preformed shape. In a preferred embodiment, middle section 95b can also include a plurality of subsections 95d, 95e and 95f, each of which is made of a different material(s) with varying degrees of firmness, rigidity or flexibility to provide improved maneuverability and ease of fastening. Distal section 95a can also be connected as at 99 to any part of an adjustable length protective sleeve 92 as shown in FIGS. 10a, 10b, 10c and 10d.

FIG. 10f shows another embodiment of protective sleeve 92 includes a connector mechanism 101, such as a self-sticking adhesive 103 along one edge 105 of a sheet 107. Other connector mechanisms such as snaps 111 may be used along corresponding edges 105 and 113. "Ziploc tracking" 109, such that a protective sleeve 92 may be formed circumferentially situated around catheter 90 by the practitioner at any time during or after the catheterization procedure.

Embodiments of the invention with protective sleeves as described above provide important advantages over previous catheterization devices and methods, including:

removal of tension on catheter 90 at the site of insertion;

secure immobilization of the catheter 90 and protective sleeve at all times;

repositioning and immobilizing catheter 90 in a sterile environment while maintaining the integrity of the catheter. This feature is especially important for catheters with small lumens or catheters which include thin conduit fibers which may be damaged by current crimping mechanisms used to immobilize the catheters within a protective sleeve.

Figure 15:
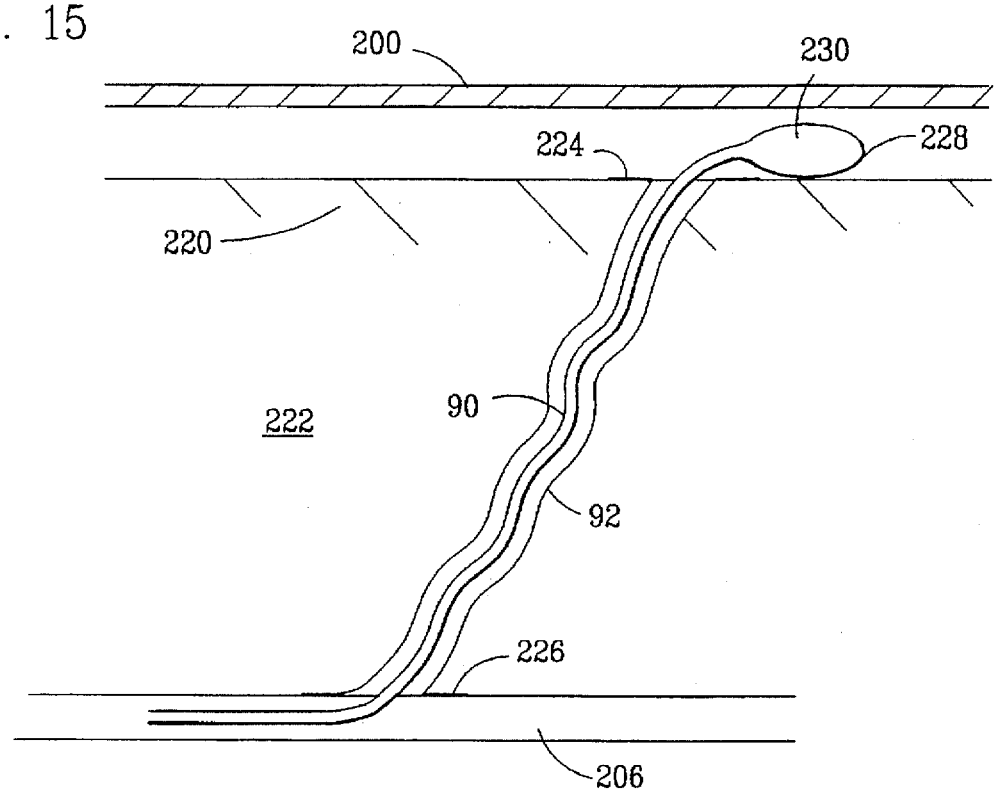
FIG. 15 is a side view of another embodiment of the invention, including a protective sleeve which encompasses a catheter connected to a subcutaneous reservoir.

FIG. 15 shows a catheter 90 within a body cavity 222. For illustrative purposes, catheter 90 is shown entering a blood vessel 206. Catheter 90 is partially or fully encompassed by protective sleeve 92 which may include proximal tabs 224 or other means for securing said protective sleeve to a part of the body wall 220 and distal tabs 226 or other means for securing the protective sleeve to tissue at or adjacent to the target tissue or material. Catheter 90 is attached to a subcutaneous reservoir 228 (e.g., Medi-Port) located under skin 200. This embodiment of a catheterization instrument allows the practitioner to use a chamber 230 of the subcutaneous reservoir 228 to insert substances into, or withdraw material from, blood vessel 206 with ease, while ensuring that the catheter 90 is both firmly immobilized and also protected by protective sleeve 92 from damage by surrounding tissue or organs.

Figure 16:
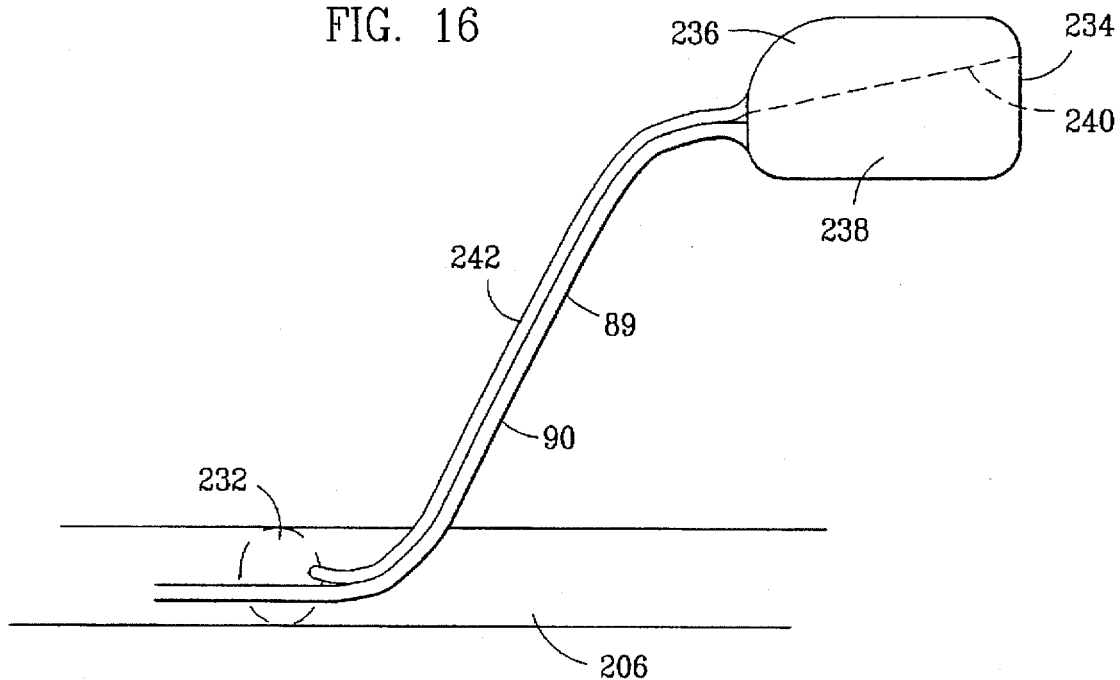
FIG. 16 is a side schematic view of an embodiment of the instrument in FIG. 15 wherein the catheter includes a balloon and the subcutaneous reservoir has a septum creating two non-communicating chambers in the reservoir.

FIG. 16 shows a catheter 90, one end of which includes a balloon 232. The catheter is in communication with blood vessel 206. The other end of catheter 90 is attached to a reservoir 234 (e.g., Medi-Port). Reservoir 234 may be subcutaneous and is advantageously partitioned into two non-communicating chambers 236 and 238 by septum 240. The first chamber 236 communicates with balloon 232 through a designated lumen 242 and is used to inflate or deflate the balloon 232. The second chamber 238 communicates with lumen 89 of catheter 90 and is used to insert substances into, or withdraw material from, blood vessel 206. One of the preferred methods requires that, prior to inserting substances (e.g., chemotherapeutic agents) into the blood vessel 206 entering or leaving malignant tissue or tumors, the practitioner temporarily limits the blood flow to or from said malignant tissue or tumor by inflating or partially inflating balloon 232. The balloon 232 is then deflated after the substances have been inserted into said blood vessels. Another method requires the use of two catheters, each with a balloon and two separate reservoirs, one catheter in the blood vessel through which blood enters the malignant tissue or tumor, and the other catheter in the blood vessel through which blood leaves the malignant tissue or tumor.

Figure 21:
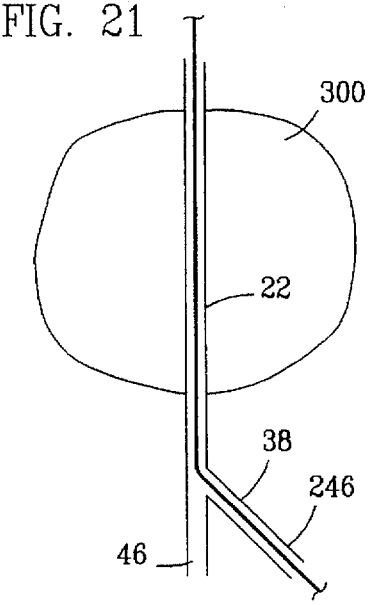
FIG. 21 is a sectional view of an embodiment of the invention that can be used for the insertion of a wire to induce hyperthermia or freeze a tumor.
Figure 22:
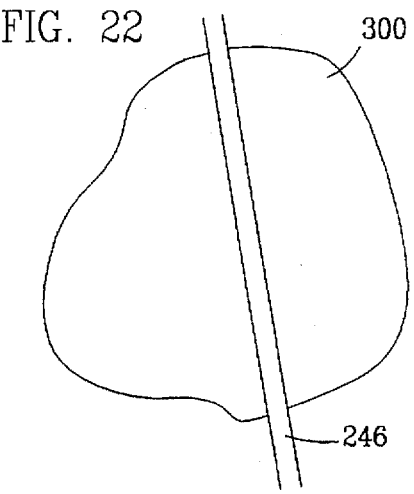
FIG. 22 is a sectional side view of the wire of FIG. 21 in place in the tumor.

Referring to FIGS. 21 and 22, if the practitioner desires to treat a tumor 300 using hyperthermia or freezing of tissue, this is easily done using the invention. The needle 22 is used to penetrate tumor 300, and a wire 246 for hyperthermia or freezing of tissue is inserted through "Y" chamber 27. This embodiment allows the practitioner to use minimally invasive procedures for discriminatory methods of treatment.

Figure 23:
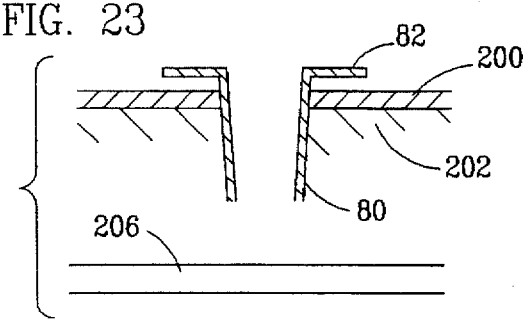
FIG. 23 is a partial sectional side view of an embodiment of a sheath in place according to the present invention.

FIG. 23 is a sectional view of a sheath 80, shown inserted through a first tissue, such as skin 200 and subcutaneous tissue 202. Sheath 80 can include tabs 82 or other means for grasping, maneuvering, or securing said sheath at the site of insertion. Advantageously and uniquely, sheath 80 does not communicate at all with the target tissue or material 206 at the catheterization site.

Figure 24:
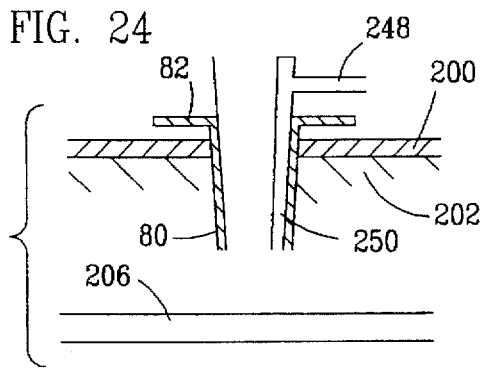
FIG. 24 is a partial sectional side view of an alternative embodiment of a sheath wherein the sheath has a lumen and a side-port.

FIG. 24 is a sectional view of an alternative embodiment of a sheath 80, including a side-port 248 which communicates with a lumen 250. Side-port 248 can be used to insert substances (e.g., antibiotics or other agents) or to withdraw tissues or materials via lumen 250.

Figure 25:
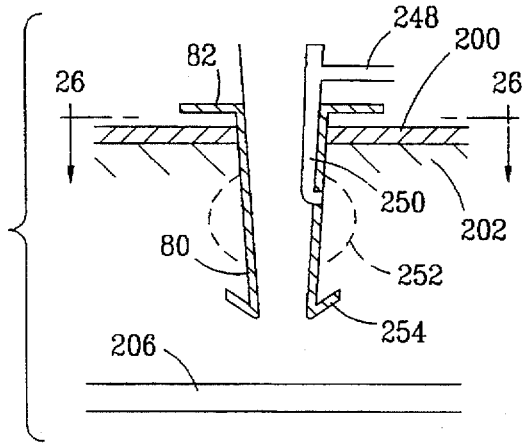
FIG. 25 is a partial sectional side view of another alternative embodiment of a sheath wherein the sheath includes a balloon.
Figure 26:
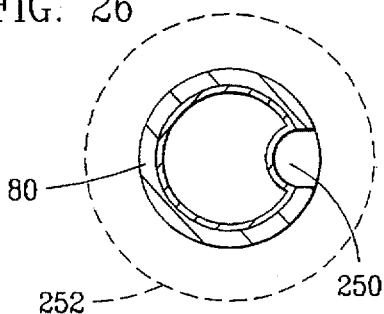
FIG. 26 is a partial sectional top view of the sheath depicted in FIG. 25 taken along line 26—26.

FIG. 25 is a sectional view of an embodiment of sheath 80 which includes a side-port 248 communicating with lumen 250. Lumen 250 also communicates with a balloon 252 which is positioned under skin 200. The practitioner can inflate balloon 252 as necessary to further secure and immobilize sheath 80. Other devices such as flanges 254 can be used to perform the function of balloon 252.

Connecting devices, particularly those used to attach components in the medical field, can often easily disengage and result in serious, possibly lethal, consequences. This invention substantially corrects the problem.

Figure 27:
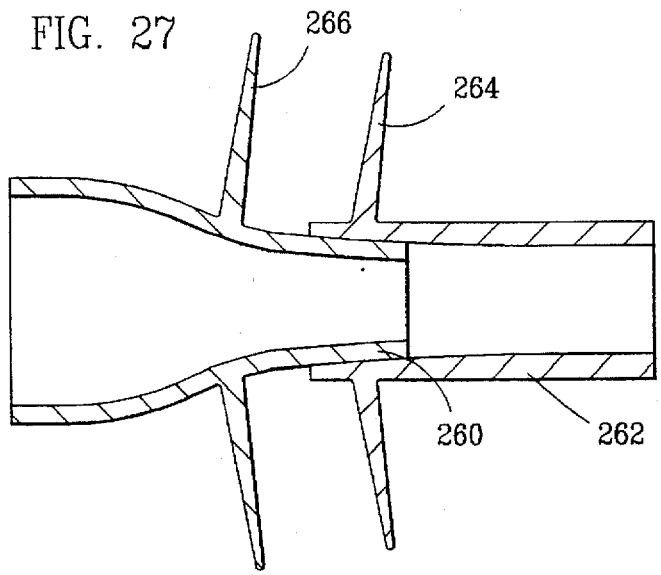
FIG. 27 is a partial section side view of a preferred embodiment of a connector system for use according to the invention.

FIG. 27 shows connecting ends 260 and 262 of catheterization system components. Projections 264 extend from connecting end 262 and projections 266 extend from connecting end 260. The projections 264 and 266 may be attached to each other using any means (e.g., a snap or twist mechanism) to ensure secure immobilization of said connecting ends 260 and 262.

Figure 28:
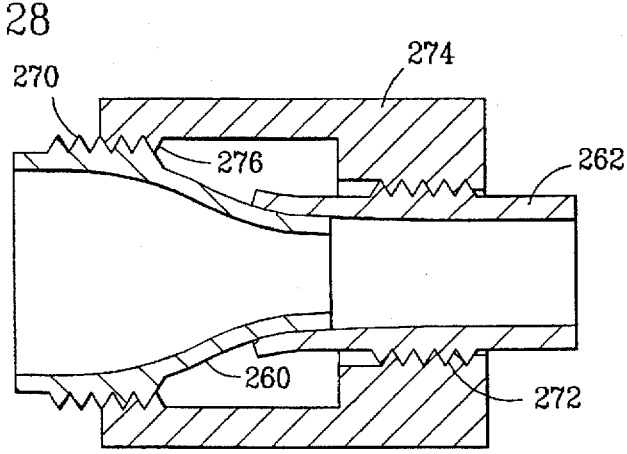
FIG. 28 is a partial section side view of another embodiment of the connector system depicted in FIG. 27.
Figure 29:
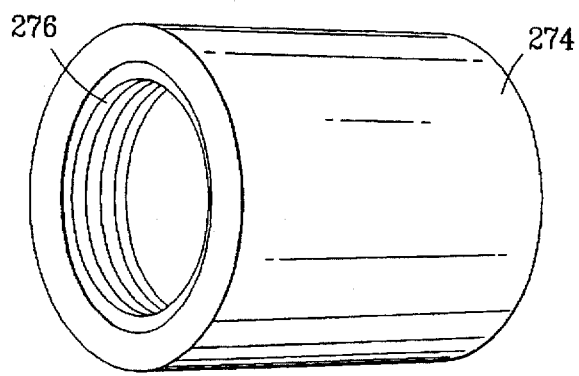
FIG. 29 is a partial sectional side view of a part of the connector depicted in FIG. 28.

FIG. 28 is an embodiment of the connector system of a catheterization wherein connecting end 260 has threads 270 and connecting end 262 has threads 272. A movable coupler member 274 is incorporated over connecting ends 260 and 262 so that the threads 270 and 272 engage said movable member which has threads 276 as shown schematically in FIG. 28. This embodiment allows improved immobilization of connecting ends 260 and 262. Other means (e.g., sliding member) for securing of connecting ends 260 and 262 might also be used instead of the threaded coupler 274 as shown.

Figure 30:
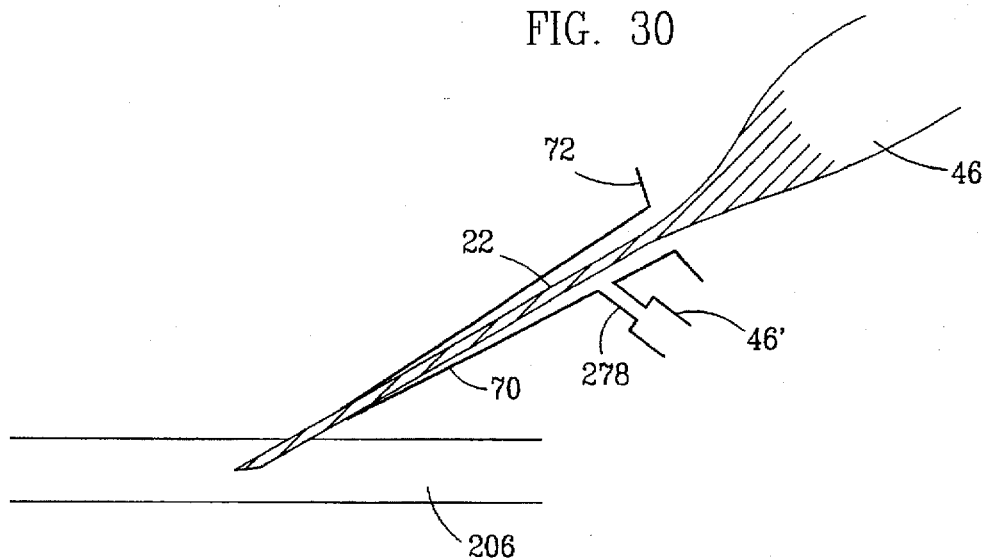
FIG. 30 is a schematic sectional side view of one embodiment of the invention showing a needle and dilator combination where the needle is inserted in the lumen of a blood vessel.
Figure 31:
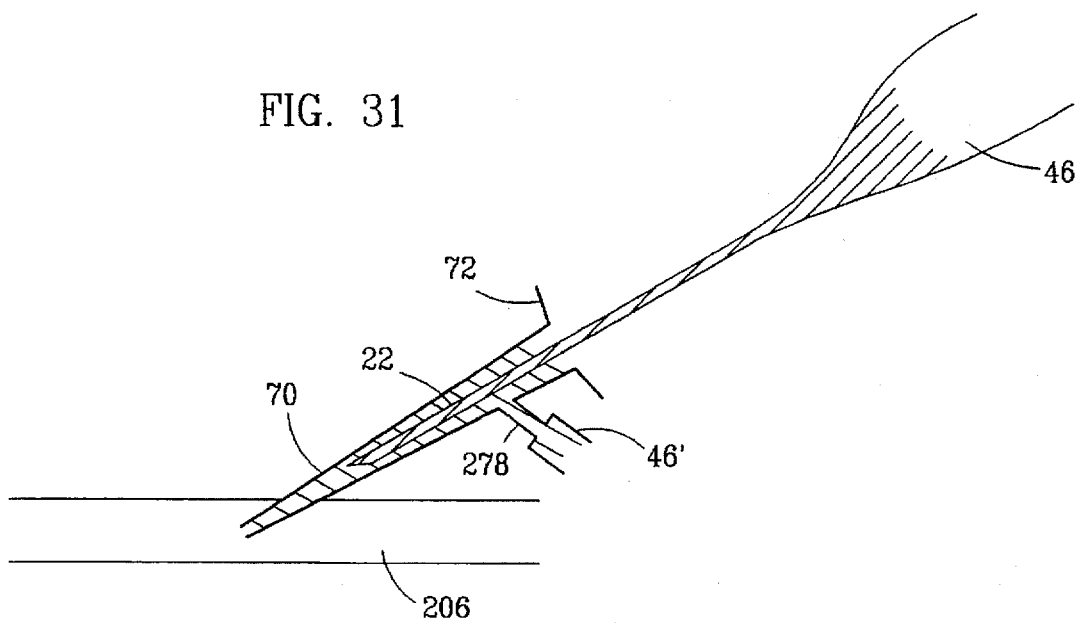
FIG. 31 is a schematic sectional side view of the system of FIG. 30 in which the needle is being withdrawn.

Using prior methods of catheterization, when a dilator is inserted into a blood vessel and the guide-wire is in place, the practitioner observes limited "flashback" because the lumen of the dilator is almost totally occluded by the guide-wire. Consequently, there is a risk that the practitioner can perforate the wall of the blood vessel while dilating the puncture site. This problem is substantially eliminated using an embodiment of the invention as shown in FIGS. 30 and 31 which show perspective views of an advantageous method according to the invention. The guide-wire is not shown for clarity. FIG. 30 shows needle 22 in place in blood vessel 206. Dilator 70 is circumferentially disposed around needle 22. Chamber or syringe 46 is attached to needle 22 to allow continuous observation of "flashback." Dilator 70 has a side-port 278 which communicates with the lumen of the dilator 70. Side-port 278 is attached to another reversibly aspiratable chamber or syringe 46' to allow observation of "flashback" when dilator 70 has been slid over needle 22 into blood vessel 206 as shown in FIG. 31. As a result, the practitioner can safely dilate the puncture site while continuously confirming that the tip of the dilator 70 is located within the lumen of the blood vessel 206. Dilator 70 can include tabs 72 or other means of maneuvering, grasping or securing dilator 70.

This invention allows catheterization to be performed anywhere on or in the body (i.e., it is universal); any type of catheterization can be accomplished (i.e, it is uniform); diagnosis and treatment can be performed at the same time using one procedure; all or selected components may be used depending on the purpose of catheterization, (i.e., the invention is comprehensive); discriminatory treatment is allowed with minimal or no hospitalization; risk to the patient is reduced; cost to the patient as well as to the health-care industry is reduced; the invention improves the quality of life for the patient and should increase his or her length of survival; and catheterization is achieved using the invention described herein and claimed below without the multiple problems discussed in the BACKGROUND OF THE INVENTION.

Whereas the present invention has been described with respect to specific embodiments thereof, it will be understood that various changes and modifications will be suggested to one skilled in the art and the invention is intended to encompass such changes and modifications as fall within the scope of the appended claims.

What is claimed is:

1. An instrument for inserting or removing substances or devices into or from a target tissue or material comprising:
   (a) a needle having an elongated shaft with at least one lumen, including a distal portion for insertion into said target tissue or material to a depth and a proximal portion which remains outside said target tissue or material into which said distal portion is inserted;
   (b) a position-sensitive feature formed at a predetermined location not solely dependent on the depth of insertion of said needle on the distal portion of said needle; and
   (c) distinctive mark associated with said proximal portion of said needle at a fixed position relative to said location of said position-sensitive feature, which indicia is observable outside of said tissue or material into which said distal portion of said needle is to be inserted and by which indicia said predetermined location of said position-sensitive feature formed at said distal portion of said needle is indicated.

2. The instrument of claim 1 wherein:
   (a) said position-sensitive feature formed on said distal portion of said needle is a beveled needle end; and
   (b) said distinctive mark is associated with said proximal portion of said needle in a fixed relationship to said angled direction of said bevel by which said direction of said bevel end may be observed from outside of said target tissue or material.

3. An instrument as in claim 1 further comprising:
   (a) a first and a second lumen extending longitudinally inside of said elongated hollow needle shaft;
   (b) wherein a relative position of said first lumen with respect to said second lumen is said position-sensitive feature of the distal portion of said needle; and
   (c) said distinctive mark is associated with said proximal portion of said needle in a fixed position with respect to said relative position of said first and second lumens, and said distinctive mark may be observed from outside of the tissue or material into which the instrument is inserted so that said relative position of said first and second lumens is indicated.

4. The instrument of claim 1 wherein:
   (a) said position-sensitive feature comprises a bent portion of said distal portion of said elongated needle; and
   (b) said distinctive mark is associated with said proximal portion of said needle in a fixed position relative to a direction of said bent distal portion, which indicia is observable from outside of said tissue or material into which said needle is inserted so that said bent direction is indicated.

5. A "Y" chamber and needle assembly for insertion or withdrawal of substances, devices, tissue, or material, comprising:
   (a) a needle having first and second longitudinal lumens and a connection hub, said longitudinal needle lumens in communication with said substances, devices, tissue or material; and
   (b) a "Y" chamber detachably connected to said needle thereto, said "Y" chamber including a first lumen of said needle having an opening in communication with said first lumen of said needle, and said "Y" chamber further including at least one side arm connected to said first lumen of said "Y" chamber, each said at least one side arm having a second lumen of said "Y" chamber with a separate entry opening and said second lumen of said "Y" chamber in communication with said second lumen of said needle detachably connected to said connection hub for communication with said needle.

6. The "Y" chamber and needle assembly of claim 5 wherein said "Y" chamber includes a plurality of lumens, and said needle includes a corresponding plurality of lumens, said needle attachable to said "Y" chamber so that said corresponding lumens in said "Y" chamber and in said needle are aligned.

7. The "Y" chamber and needle assembly as in claim 5 further comprising at least one self-sealing device interposed in at least one of said lumens of said "Y" chamber and needle assembly for restricting movement of substances therethrough.

8. The "Y" chamber of claim 7 wherein said self-sealing device comprises a one-way valve restricting movement of substances in at least one longitudinal direction.

9. A "Y" chamber as in claim 7 wherein said self-sealing device comprises a self-sealing grommet formed of a resilient material such that a device may be inserted therethrough and such that said grommet automatically closes upon removal of said device.

10. An instrument for facilitating catheterization comprising:
    (a) a needle having a substantially uniform diameter for puncturing a tissue or material to be catheterized;
    (b) a dilator having an exterior diameter increasing from a distal portion to a proximal portion and circumferentially disposed around said needle for expanding said punctured tissue or material so that catheterization is facilitated;
    (c) a distal portion and a proximal portion of said needle and at least one lumen extending through said needle between said distal and proximal portions; and (d) at least one "Y" chamber attached to said proximal portion of said needle in fluid communication with one of said at least one lumen and for insertion or removal of substances or devices therethrough.

11. A instrument for facilitating catheterization comprising:
   (a) a needle having a smoothly tapered surface with a distal portion smaller than a proximal portion; and
   (b) a dilator having an exterior diameter increasing from a distal portion to a proximal portion circumferentially disposed around said needle for expanding said punctured tissue or material so that catheterization is facilitated.

12. An instrument for facilitating catheterization as in claim 11 further comprising:
   (a) a distal portion and a proximal portion of said needle and at least one lumen extending through said needle between said distal and proximal portions; and
   (b) at least one "Y" chamber attached to said proximal portion of said needle in fluid communication with one of said at least one lumen and for insertion or removal of substances or devices therethrough.

13. An instrument for facilitating catheterization as in claim 10 or 11 further comprising:
   (a) a catheter or catheterization device operatively associated with said needle and said dilator having a diameter sized and adapted for insertion into said target tissue or material expanded by said dilator when said dilator is removed from target tissue; and
   (b) a protective sleeve at least partially encompassing said catheter or catheterization device.

14. An instrument for facilitating catheterization as in claim 11 further comprising:
   (a) a catheter or catheterization device sized for insertion into tissue or material expanded by said dilator; and
   (b) a protective sleeve at least partially encompassing said catheter or catheterization device exterior to said tissue or material.

15. A device as in claim 10 or 11 further comprising an at least reversibly aspiratable chamber connected to said needle to allow detection of tissue or material or insertion of substances.

16. An instrument for catheterization comprising:
   (a) a needle for puncturing a target tissue or material to be catheterized;
   (b) a "Y" chamber attached to said needle for insertion or removal of substances or devices to or from said target tissue or material to be catheterized and through said needle and said "Y" chamber;
   (c) a catheter or catheterization device operatively associated with said instrument for catheterization adapted to be at least partially insertable into said target tissue or material after it is punctured by said needle; and
   (d) a protective sleeve, at least partially encompassing said catheter or catheterization device without contacting said target tissue.

17. The catheterization instrument of claim 16 further comprising a guide-wire for insertion through said "Y" chamber and said needle into said target tissue or material for facilitating insertion of said catheter or catheterization device into said target tissue or material.

18. The instrument as in claim 16 further comprising a reversibly aspiratable chamber in fluid communication with said needle to allow detection of tissue or material or insertion of substances.

19. A kit for use in a catheterization procedure comprising:
   (a) a needle with a substantially uniform diameter for puncturing a tissue or material which is the target of catheterization;
   (b) a dilator having an exterior diameter increasingly sized and adapted for engagement over said needle circumferentially disposed around said needle for expanding said punctured tissue or material which is the target of catheterization; and
   (c) at least one "Y" chamber constructed to be attachable to a proximal portion of said needle for insertion or removal of substances or devices therethrough.

20. A kit for use in a catheterization procedure comprising:
   (a) a needle with a tapered shaft having a distal end smaller than a proximal end for puncturing a tissue or material which is the target of catheterization; and
   (b) a dilator having an exterior diameter increasingly sized for engagement over said needle circumferentially disposed around said needle for expanding said punctured tissue or material which is the target of catheterization.

21. A kit for use in a catheterization procedure as in claim 20 further comprising at least one "Y" chamber attachable to a proximal portion of said needle for insertion or removal of substances or devices therethrough.

22. A kit for use in a catheterization procedure as in claim 12 or 21 further comprising:
   (a) a catheter or catheterization device having a diameter sized and adapted for insertion into said punctured and expanded tissue or material which is the target of catheterization when said dilator is removed from said punctured and expanded tissue or material; and
   (b) a protective sleeve at least partially encompassing said catheter or catheterization device without containing said tissue or material which is the target of catheterization.

23. A kit for use in a catheterization procedure as in claim 20 further comprising:
   (a) a catheter or catheterization device sized and adapted for insertion into said punctured tissue or material expanded by said dilator when said dilator is removed from said punctured and expanded tissue or material; and
   (b) a protective sleeve at least partially encompassing said catheter or catheterization device along a portion thereof which is exterior to said tissue or material which is the target of catheterization.

24. A kit for use in a catheterization procedure as in claim 20 further comprising a guide-wire insertable through said needle into said tissue or material and by which insertion of a device used for catheterization into said tissue or material is facilitated.

25. A kit as in claim 20 further comprising a reversibly aspiratable chamber in fluid communication with said needle to allow detection of tissue or material or insertion of substances.

26. A kit for catheterization of a target tissue or material comprising:
   (a) a needle for insertion into a tissue or material which is the target of catheterization;
   (b) a "Y" chamber attached to said needle for insertion or removal of substances or devices from said tissue or material which is the target of the catheterization through said needle and said "Y" chamber;

(c) a catheter or catheterization device at least partially insertable into said target tissue or material into which said needle has been inserted; and (d) a protective sleeve at least partially encompassing said catheter or catheterization device.

27. A kit for catheterization as in claim 26 further comprising a guide-wire for insertion through said "Y" chamber and said needle into said target tissue or material for facilitating insertion of said catheter or catheterization device into said target tissue or material.

28. A kit as in claim 26 further comprising a reversibly aspiratable chamber in fluid communication with said needle to allow detection of tissue or material or insertion of substances.

29. A kit for catheterization of a target tissue or material comprising:

(a) a hollow tubing for use in inserting or withdrawing substances or devices from the target tissue or material to be catheterized;

(b) a "Y" chamber attachable to said hollow tubing through which substances or devices may be inserted or tissue or material withdrawn through said hollow tubing which is in communication with said target tissue or material;

(c) a catheter or catheterization device operatively associated with said hollow tubing for communicating with said target tissue; and (d) a protective sleeve for at least partially encompassing said catheter or catheterization device at a point thereon which is exterior to said tissue or material which is the target of catheterization.

30. A kit for use in catheterization as in claim 29 further comprising a guide-wire insertable through said "Y" chamber and insertable through said hollow tubing and into said target tissue or material to facilitate catheterization.

31. A kit as in claim 29 further comprising a reversibly aspiratable chamber attachable in fluid communication with said hollow tubing to allow detection of tissue or material or insertion of substances.

32. A method for catheterization of a tissue or material which is the target of catheterization comprising the steps of:

(a) circumferentially disposing a dilator around a needle;

(b) inserting said needle into said target tissue or material;

(c) sliding said dilator along said needle into said tissue or material to be catheterized for expanding said tissue or material so that catheterization is facilitated; and (d) using a "Y" chamber for insertion of substances or devices or removal of tissue or material through said needle.

33. A method as in claim 32 further comprising the steps of:

(a) inserting a catheter or catheterization device into the target tissue or material to be catheterized; and (b) at least partially encompassing said catheter or catheterization device with a protective sleeve exterior to said tissue or material.

34. A method as in claim 32 further comprising the step of inserting a guide-wire through said needle and dilator and into said tissue or material which is the target of catheterization thereby facilitating insertion of said catheter or catheterization device.

35. A method as in claim 32 further comprising a step of reversibly aspirating fluid in communication with said needle into a reversibly aspiratable chamber to allow detection of tissue or material or for insertion of substances.

36. A method for catheterization of a target tissue or material comprising the steps of:

(a) puncturing said target tissue or material for catheterization with a hollow needle;

(b) inserting a catheter or catheterization device through a "Y" chamber which is attached to said hollow needle and thence into said punctured tissue or material which is the target of catheterization; and (c) partially encompassing said catheter or catheterization device with a protective sleeve exterior to said tissue or material which is the target of catheterization.

37. A method as in claim 36 further comprising the steps of:

(a) circumferentially disposing a dilator around said hollow needle; and (b) sliding said circumferentially disposed dilator along said hollow needle and thereby expanding said punctured target tissue or material.

38. A method as in claim 36 further comprising a reversibly aspiratable chamber in fluid communication with said needle to allow detection of tissue or material or insertion of substances.

39. A method of catheterization comprising the steps of:

(a) inserting a guide-wire through a "Y" chamber and then into said target tissue or material;

(b) inserting a catheter or other catheterization device along said guide-wire into said target tissue or material; and (c) at least partially encompassing said catheter or catheterization device with a protective sleeve.

40. A device as in claim 11 or 15 wherein:

(a) said needle further comprises a position-sensitive feature on a distal portion thereof not solely dependent on the depth of insertion of said needle; and (b) distinctive mark associated with a proximal portion of said needle in a fixed spatial relationship with respect to said position-sensitive feature such that said distinctive mark can be observed when the needle is inserted into said target tissue or material so that the position of said position-sensitive feature is indicated.

41. A kit as in claim 20 or 26 wherein:

(a) said needle further includes a position-sensitive feature at a distal portion thereof not solely dependent on the depth of insertion of said needle; and (b) further comprising a distinctive mark associated with a proximal portion of said needle in a fixed relative position with respect to said position-sensitive feature so that observation of said distinctive mark outside of said target tissue or material indicates the position of said position-sensitive feature.

42. A kit as in claim 29 wherein:

(a) said hollow tubing further comprises a position-sensitive feature at a distal portion thereof not solely dependent on the depth of insertion of said hollow tubing; and (b) further comprising a distinctive mark associated with a proximal portion of said hollow tubing in a fixed relative position with respect to said position-sensitive feature so that observation of said distinctive mark outside of said target tissue or material indicates the position of said position-sensitive feature.

43. An instrument for facilitating catheterization as in claims 11 or 16 wherein a self-sealing device is interposed with an elongated lumen in said needle for restricting movement of substances in at least one longitudinal direction through said lumen of said needle.

44. A kit for use in a catheterization procedure as in claims 20 or 26 wherein:
   (a) said needle further comprises at least one lumen extending longitudinally therethrough; and
   (b) further comprising a self-sealing device interposable within said elongated lumen for restricting movement of substances in at least one longitudinal direction through said lumen of said needle.

45. A device for catheterization of a target tissue or material comprising a dilator including at least one side-port for infusion or withdrawal of substances or devices into or from said target tissue or material through said dilator and said side-port, further comprising a self-sealing device interposed within an elongated lumen formed in said dilator, said self-sealing device for restricting movement of substances in at least one longitudinal direction therethrough.

46. A kit for catheterization as in claim 29 further comprising a self-sealing device interposed within said hollow tubing for restricting movement of substances in at least one longitudinal direction therethrough.

47. An instrument for facilitating catheterization comprising:
   (a) a needle having a substantially uniform diameter for puncturing a tissue or material to be catheterized;
   (b) a dilator having an exterior diameter increasing from a distal portion to a proximal portion and circumferentially disposed around said needle for expanding said punctured tissue or material so that catheterization is facilitated;
   (c) a catheter or catheterization device operatively associated with said instrument and sized and adapted for insertion into tissue or material expanded by said dilator after said dilator is removed; and
   (d) a protective sleeve at least partially encompassing said catheter or catheterization device exterior to said tissue or material.

48. An instrument for facilitating catheterization comprising:
   (a) a needle having a substantially uniform diameter for puncturing a tissue or material to be catheterized;
   (b) a dilator having an exterior diameter increasing from a distal portion to a proximal portion and circumferentially disposed around said needle for expanding said punctured tissue or material so that catheterization is facilitated; and
   (c) an at least reversibly aspiratable chamber connected to said needle to allow detection of tissue or material or insertion of substances.

49. A kit for use in a catheterization procedure comprising:
   (a) a needle with a substantially uniform diameter for puncturing a tissue or material which is the target of catheterization;
   (b) a dilator having an exterior diameter increasingly sized and adapted for engagement over said needle and circumferentially disposed around said needle for expanding said punctured tissue or material which is the target of catheterization;
   (c) a catheter or catheterization device sized and adapted for insertion into said punctured tissue or material expanded by said dilator when said dilator is removed from said tissue; and
   (d) a protective sleeve at least partially encompassing said catheter or catheterization device along a portion thereof which is exterior to said tissue or material which is the target of catheterization.

50. A kit for use in a catheterization procedure comprising:
   (a) a needle with a substantially uniform diameter for puncturing a tissue or material which is the target of catheterization;
   (b) a dilator having an exterior diameter increasingly sized and adapted for engagement over said needle circumferentially disposed around said needle for expanding said punctured tissue or material which is the target of catheterization; and
   (c) a guide wire insertable through said needle into said tissue or material and by which insertion of a device used for catheterization into said tissue or material is facilitated.

51. A kit for use in a catheterization procedure comprising:
   (a) a needle with a substantially uniform diameter for puncturing a tissue or material which is the target of catheterization;
   (b) a dilator having an exterior diameter increasingly sized and adapted for engagement over said needle and circumferentially disposed around said needle for expanding said punctured tissue or material which is the target of catheterization; and
   (c) a reversibly aspiratable chamber in fluid communication with said needle to allow detection of tissue or material or insertion of substances.

52. An instrument for facilitating catheterization comprising:
   (a) a needle having a substantially uniform diameter for puncturing a tissue or material to be catheterized;
   (b) a dilator having an exterior diameter increasing from a distal portion to a proximal portion and circumferentially disposed around said needle for expanding said punctured tissue or material so that catheterization is facilitated;
   (c) said needle further comprising a position-sensitive feature on a distal portion thereof not solely dependent on the depth of insertion of said needle; and
   (d) a distinctive mark associated with a proximal portion of said needle in a fixed spatial relationship with respect to position-sensitive feature such that said distinctive mark can be observed when the needle is inserted into said target tissue or material so that the position of the position-sensitive feature is indicated by said distinctive mark.

53. A kit for use in a catheterization procedure comprising:
   (a) a needle with a substantially uniform diameter for puncturing a tissue or material which is the target of catheterization;
   (b) a dilator having an exterior diameter increasingly sized for engagement over said needle and circumferentially disposed around said needle for expanding said punctured tissue or material which is the target of catheterization;
   (c) said needle further including a position-sensitive feature at a distal portion thereof not solely dependent on the depth of insertion of said needle; and
   (d) a distinctive mark associated with a proximal portion of said needle in a fixed relative position with respect to said position-sensitive feature so that observation of said distinctive mark outside of said target tissue or material indicates the position of said position-sensitive feature.

54. An instrument for facilitating catheterization comprising:
   (a) a needle having a substantially uniform diameter for puncturing a tissue or material to be catheterized;
   (b) a dilator having an exterior diameter increasing from a distal portion to a proximal portion and circumferentially disposed around said needle for expanding said punctured tissue or material so that catheterization is facilitated; and
   (c) a self-sealing device interposed within an elongated lumen in said needle for restricting movement of substances in at least one longitudinal direction through said lumen of said needle.

55. A kit for use in a catheterization procedure comprising:
   (a) a needle with a substantially uniform diameter for puncturing a tissue or material which is the target of catheterization;
   (b) a dilator having an exterior diameter increasingly sized and adapted for engagement over said needle and circumferentially disposed around said needle for expanding said punctured tissue or material which is the target of catheterization;
   (c) said needle further comprising at least one elongated lumen extending longitudinally therethrough; and
   (d) a self-sealing device interposed within said elongated lumen for restricting movement of substances in at least one longitudinal direction through said lumen of said needle.

* * * * *

UNITED STATES PATENT AND TRADEMARK OFFICE
CERTIFICATE OF CORRECTION

PATENT NO. : 5,695,479

DATED : December 9, 1997

INVENTOR(S) : Ravindar Jagpal

It is certified that error appears in the above-identified patent and that said Letters Patent are hereby corrected as shown below:

In the Notice:

that portion of the Notice reading "November 2, 2 010" should read -- the expiration of U.S. Patent No. 5,257,979--

Signed and Sealed this

Tenth Day of October, 2000

*Attest:*

Q. TODD DICKINSON

*Attesting Officer*                    *Director of Patents and Trademarks*